US00RE49784E

(19) United States
(12) Reissued Patent
Ren et al.

(10) Patent Number: US RE49,784 E
(45) Date of Reissued Patent: Jan. 2, 2024

(54) APPARATUS OF PLURAL CHARGED-PARTICLE BEAMS

(71) Applicant: ASML Netherlands B.V., Veldhoven (NL)

(72) Inventors: Weiming Ren, San Jose, CA (US); Xuedong Liu, San Jose, CA (US); Xuerang Hu, San Jose, CA (US); Zhong-wei Chen, San Jose, CA (US)

(73) Assignee: ASML Netherlands B.V., Veldhoven (NL)

(21) Appl. No.: 17/005,212

(22) Filed: Aug. 27, 2020

Related U.S. Patent Documents

Reissue of:
(64) Patent No.: 10,062,541
Issued: Aug. 28, 2018
Appl. No.: 15/417,360
Filed: Jan. 27, 2017

U.S. Applications:
(60) Provisional application No. 62/287,626, filed on Jan. 27, 2016.

(51) Int. Cl.
*H01J 37/06* (2006.01)
*H01J 37/28* (2006.01)
(Continued)

(52) U.S. Cl.
CPC ..... *H01J 37/06* (2013.01); *G01N 23/2251* (2013.01); *H01J 37/05* (2013.01);
(Continued)

(58) Field of Classification Search
CPC ..... H01J 37/05; H01J 37/06; H01J 37/147; H01J 37/1472; H01J 37/1474; H01J 37/15;
(Continued)

(56) References Cited

U.S. PATENT DOCUMENTS 5,943,349 A * 8/1999 Ohta ..... H01S 5/141 372/20
6,943,349 B2 9/2005 Adamec et al.
(Continued)

FOREIGN PATENT DOCUMENTS

CN 102598199 A 7/2012
CN 104488064 A 4/2015
(Continued)

OTHER PUBLICATIONS

Office Action issued by the Taiwanese Patent Office in related Patent Application No. 108110284, dated Nov. 4, 2019 (7 pgs.).
(Continued)

*Primary Examiner* — James A Menefee
(74) *Attorney, Agent, or Firm* — Finnegan, Henderson, Farabow, Garrett & Dunner, LLP

(57) ABSTRACT

A new multi-beam apparatus with a total FOV variable in size, orientation and incident angle, is proposed. The new apparatus provides more flexibility to speed the sample observation and enable more samples observable. More specifically, as a yield management tool to inspect and/or review defects on wafers/masks in semiconductor manufacturing industry, the new apparatus provide more possibilities to achieve a high throughput and detect more kinds of defects.

36 Claims, 24 Drawing Sheets

(51) Int. Cl.

| | |
|---|---|
| ***H01J 37/147*** | (2006.01) |
| ***H01J 37/22*** | (2006.01) |
| ***G01N 23/2251*** | (2018.01) |
| ***H01J 37/145*** | (2006.01) |
| ***H01J 37/05*** | (2006.01) |
| ***H01J 37/244*** | (2006.01) |

(52) U.S. Cl.
CPC ..... *H01J 37/145* (2013.01); *H01J 37/1474* (2013.01); *H01J 37/226* (2013.01); *H01J 37/244* (2013.01); *H01J 37/28* (2013.01); *G01N 2223/418* (2013.01); *G01N 2223/6116* (2013.01); *H01J 2237/057* (2013.01); *H01J 2237/2448* (2013.01); *H01J 2237/2817* (2013.01)

(58) Field of Classification Search
CPC ..... H01J 37/21; H01J 2237/024; H01J 2237/0822; H01J 2237/0825; H01J 2237/15; H01J 2237/1502; H01J 2237/1508; H01J 2237/1516; H01J 2237/21
See application file for complete search history.

(56) References Cited

U.S. PATENT DOCUMENTS

| | | | | |
|---|---|---|---|---|
| 7,244,949 | B2 * | 7/2007 | Knippelmeyer | B82Y 10/00 250/396 ML |
| 9,035,249 | B1 * | 5/2015 | Frosien | H01J 37/05 250/310 |
| 9,153,413 | B2 * | 10/2015 | Almogy | H01J 37/05 |
| 9,607,805 | B2 * | 3/2017 | Liu | H01J 37/28 |
| 9,691,588 | B2 * | 6/2017 | Ren | H01J 37/28 |
| 9,922,799 | B2 * | 3/2018 | Li | H01J 37/28 |
| 10,062,541 | B2 | 8/2018 | Ren et al. | |
| 10,141,160 | B2 | 11/2018 | Ren et al. | |
| 10,236,156 | B2 | 3/2019 | Ren et al. | |
| 10,276,347 | B2 * | 4/2019 | Ren | H01J 37/1472 |
| 10,395,886 | B2 | 8/2019 | Ren et al. | |
| 10,541,110 | B2 * | 1/2020 | Li | H01J 37/10 |
| 10,643,820 | B2 * | 5/2020 | Ren | H01J 37/05 |
| 11,062,877 | B2 * | 7/2021 | Li | H01J 37/10 |
| 11,217,423 | B2 * | 1/2022 | Ren | H01J 37/28 |
| 11,302,514 | B2 * | 4/2022 | Ren | H01J 37/28 |
| 11,328,894 | B2 * | 5/2022 | Ren | H01J 37/05 |
| 2001/0010362 | A1 | 8/2001 | Simizu | |
| 2003/0168606 | A1 | 9/2003 | Adamec et al. | |
| 2004/0232349 | A1 | 11/2004 | Kruit | |
| 2009/0014649 | A1 | 1/2009 | Nakasuji et al. | |
| 2010/0213370 | A1 | 8/2010 | Nakasuji et al. | |
| 2012/0241606 | A1 | 9/2012 | Han et al. | |
| 2014/0158902 | A1 | 6/2014 | Knippelmeyer et al. | |
| 2014/0175303 | A1 | 6/2014 | Touya et al. | |
| 2015/0069235 | A1 | 3/2015 | Kemen et al. | |
| 2015/0155134 | A1 | 6/2015 | Frosien et al. | |
| 2015/0179399 | A1 | 6/2015 | Kruit et al. | |
| 2015/0270095 | A1 | 9/2015 | Kruit | |
| 2016/0267096 | A1 | 9/2016 | Zhu et al. | |
| 2016/0268096 | A1 | 9/2016 | Ren et al. | |
| 2016/0284505 | A1 * | 9/2016 | Ren | H01J 37/28 |
| 2017/0025241 | A1 | 1/2017 | Li et al. | |
| 2017/0025243 | A1 * | 1/2017 | Ren | H01J 37/06 |
| 2017/0154756 | A1 * | 6/2017 | Ren | H01J 37/14 |
| 2020/0286707 | A1 * | 9/2020 | Maassen | H01J 37/21 |
| 2022/0005665 | A1 * | 1/2022 | Ren | H01J 37/145 |

FOREIGN PATENT DOCUMENTS

| | | | |
|---|---|---|---|
| EP | 2508903 | A2 | 10/2012 |
| EP | 2854153 | A2 | 4/2015 |
| EP | 2508903 | B1 | 5/2016 |
| JP | 2005-268788 | A | 9/2005 |
| JP | 2007317467 | A | 12/2007 |
| JP | 2008008890 | A | 1/2008 |
| JP | 2009507352 | A | 2/2009 |
| JP | 2012243803 | A | 12/2012 |
| JP | 2015520501 | A | 7/2015 |
| KR | 20150035741 | A | 4/2015 |
| TW | 201248673 | A | 12/2012 |
| TW | 201250759 | A | 12/2012 |
| TW | 201610425 | A | 3/2016 |
| WO | WO 2012/128967 | A2 | 9/2012 |
| WO | WO 2016/145458 | A1 | 9/2016 |
| WO | WO 2017/015483 | A1 | 1/2017 |

OTHER PUBLICATIONS

Invitation Letter to Respond to the Written Opinion issued by the IPOS Intellectual Property Office of Singapore, in related Patent Application No. 11201806100P, dated Sep. 3, 2019 (1 pg.).
Written Opinion issued by the IPOS Intellectual Property Office of Singapore, in related Patent Application No. 11201806100P, dated Aug. 2, 2019 (7 pgs.).
Search Report issued by the IPOS Intellectual Property Office of Singapore, in related Patent Application No. 11201806100P, dated Aug. 2, 2019 (4 pgs.).
Notice for Reasons for Rejection issued by the Japanese Office Action in related Japanese Application No. 2018-538555, dated Sep. 30, 2019 (7 pgs.).
Notification of Reason(s) for Refusal issued in related Korean Patent Application No. 10-2018-7024537, dated Apr. 27, 2020 (10 pgs.).
Extended European Search Report, pursuant to Rule 62 EPC, the Supplementary European Search Report (Art. 153(7) EPC) and the European Search Opinion issued in related Patent Application No. 17744929.5, dated Sep. 20, 2019 (7 pgs.).
Office Action issued by the ROC (Taiwan) Patent Office in related Patent Application No. 106104145, dated Jul. 13, 2018 (14 pgs.).
First Chinse Office Action issued in related Chinese Patent Application No. 201780019776.X, dated Jun. 29, 2020 (10 pgs.).
International Search Report issued in related PCT Patent Application No. PCT/US17/15223, dated Jun. 5, 2017 (4 pgs.).
Notice of Reasons for Rejection issued in related Japanese Patent Application No. 2020-109028; dated Jul. 2, 2021 (6 pgs.).
Examination Report from the Intellectual Property Office of Singapore issued in related Singapore Patent Application No. 11201806100P; dated Mar. 14, 2023 (6 pgs.).
Weiming Ren et al., U.S. Appl. No. 15/065,342, filed Mar. 9, 2016, USA.
Weiming Ren et al., U.S. Appl. No. 15/078,369, filed Mar. 23, 2016, USA.
Xuedong Liu et al., U.S. Appl. No. 15/150,858, filed May 10, 2016, USA.
Shuai Li et al., U.S. Appl. No. 15/213,781, filed Jul. 19, 2016, USA.
Weiming Ren et al., U.S. Appl. No. 15/216,258, filed Jul. 21, 2016, USA.
Weiming Ren et al., U.S. Appl. No. 15/365,145, filed Nov. 30, 2016, USA.

* cited by examiner

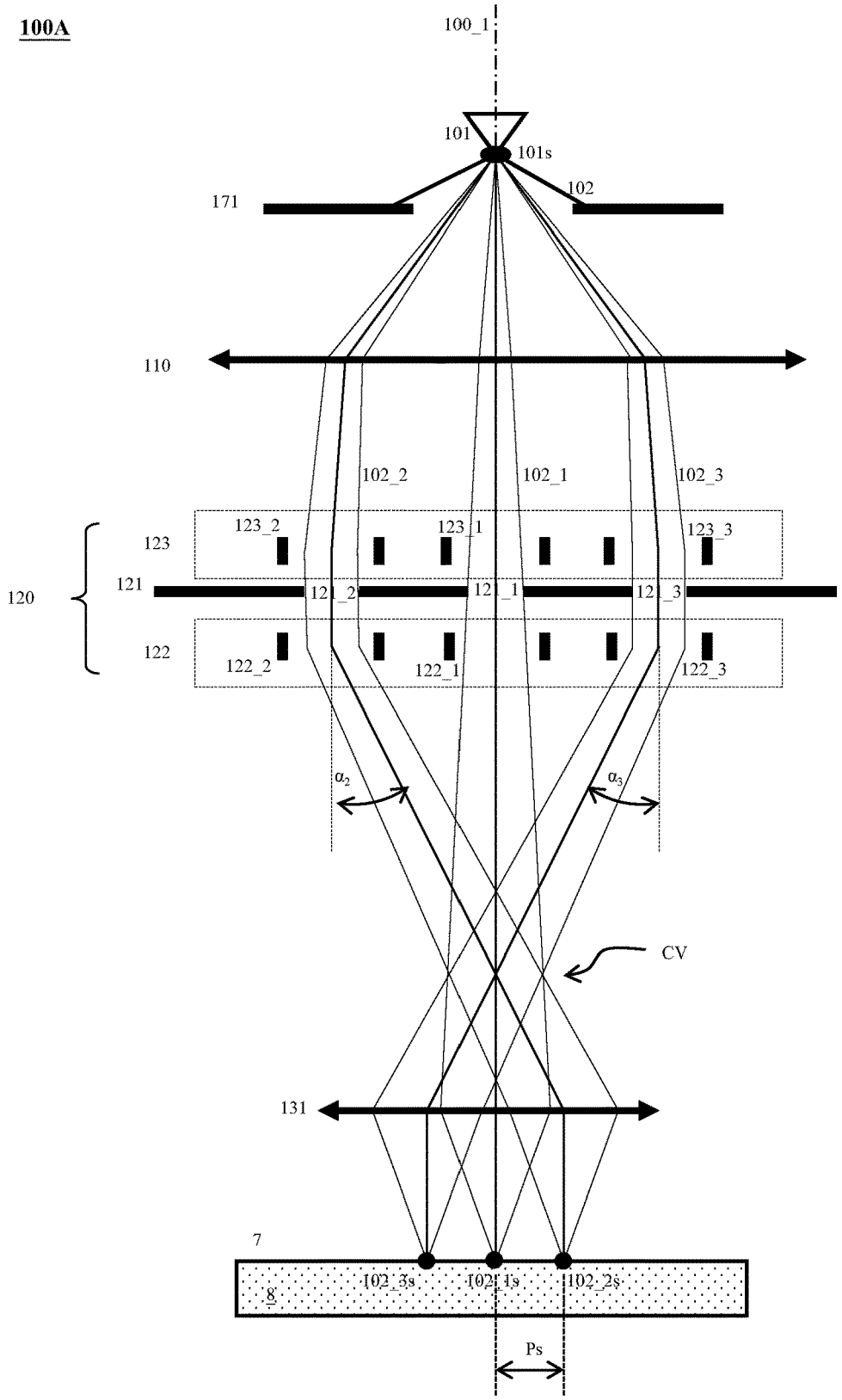
Figure 1A (Prior-Art)

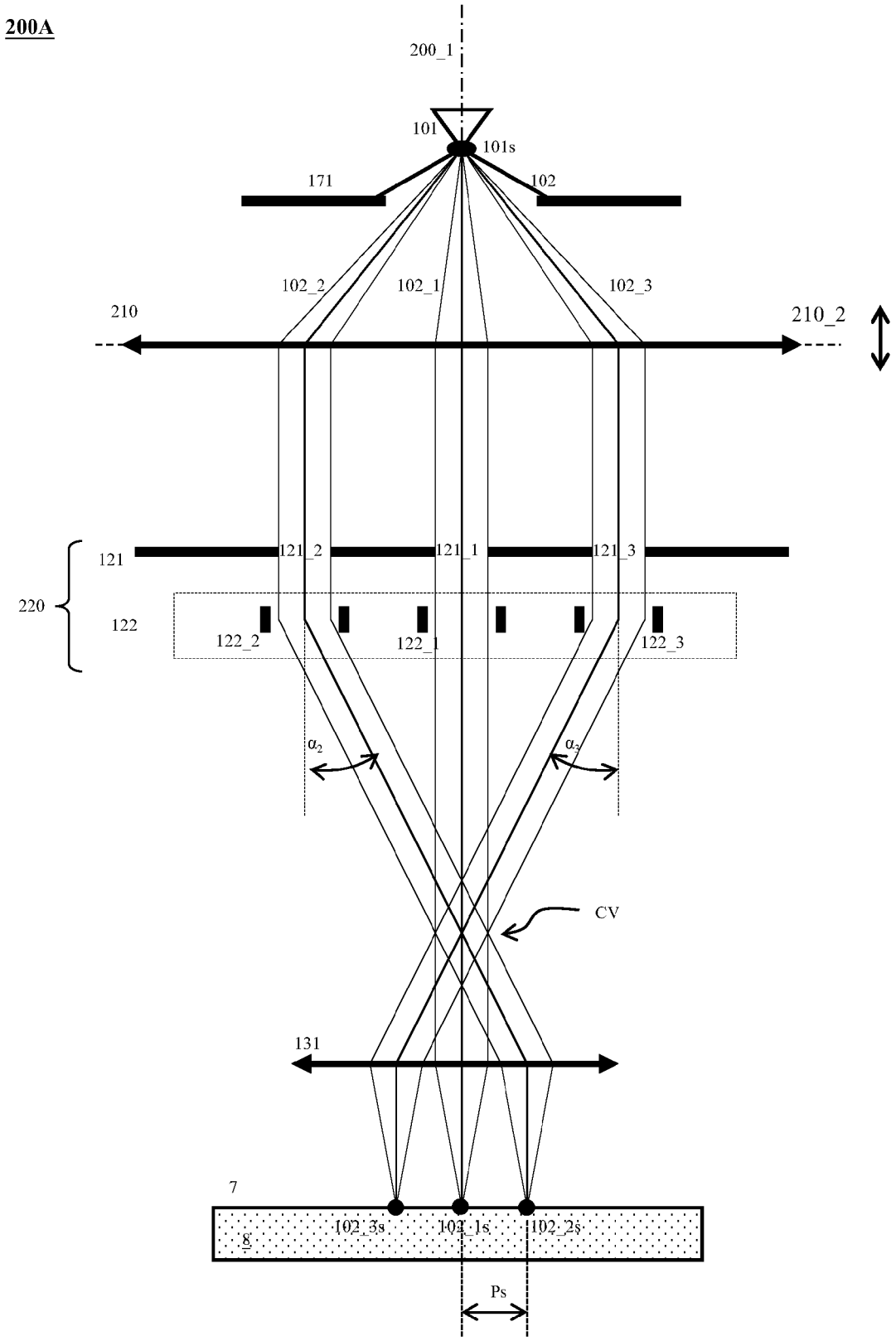
Figure 1B (Prior-Art)

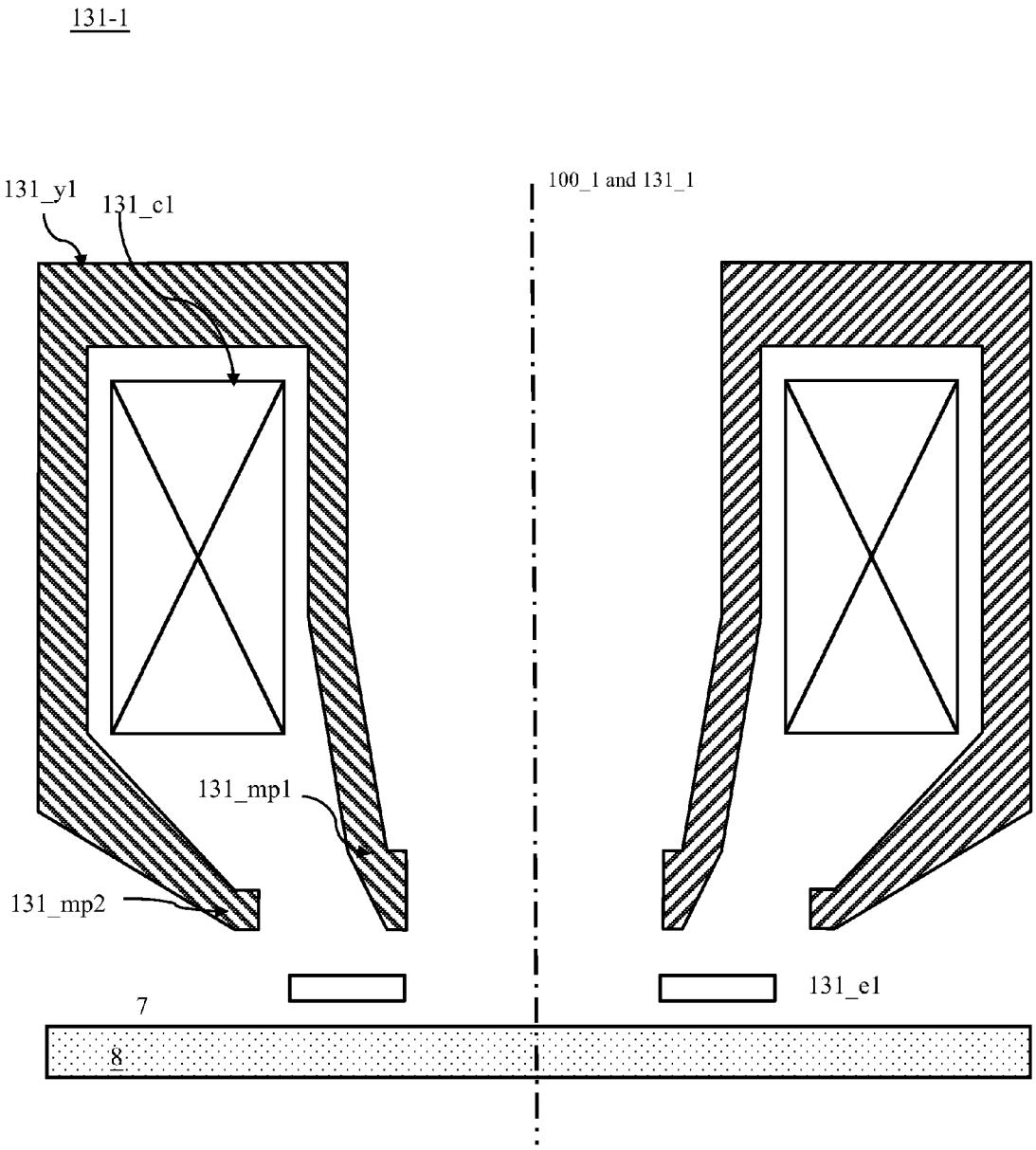
Figure 1C (Prior-Art)

631-1

631-2

631-3

APPARATUS OF PLURAL CHARGED-PARTICLE BEAMS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CLAIM OF PRIORITY

This [application] *is a reissue of U.S. Pat. No. 10,062,541 B2, issued on Aug. 28, 2018, from U.S. patent application Ser. No. 15/417,360, filed Jan. 27, 2017, which* claims the benefit of priority of U.S. provisional application No. 62/287,626 entitled to Ren et al. filed on Jan. 27, 2016 and entitled "Apparatus of Plural Charged-Particle Beams"[, the entire disclosures of which are incorporated herein by reference]. *The contents of the above-identified applications are incorporated herein by reference in their entireties.*

CROSS REFERENCE TO RELATED APPLICATIONS

This application is related to U.S. application Ser. No. 15/065,342 entitled to Ren et al. filed on Mar. 9, 2016 and entitled "Apparatus of Plural Charged-Particle Beams", the entire disclosures of which are incorporated herein by reference This application is related to U.S. application Ser. No. 15/078,369 entitled to Ren et al. filed on Mar. 23, 2016 and entitled "Apparatus of Plural Charged-Particle Beams", the entire disclosures of which are incorporated herein by reference.

This application is related to U.S. application Ser. No. 15/150,858 entitled to Liu et al. filed on May 10, 2016 and entitled "Apparatus of Plural Charged-Particle Beams", the entire disclosures of which are incorporated herein by reference.

This application is related to U.S. application Ser. No. 15/213,781 entitled to Li et al. filed on Jul. 19, 2016 and entitled "Apparatus of Plural Charged-Particle Beams", the entire disclosures of which are incorporated herein by reference.

This application is related to U.S. application Ser. No. 15/216,258 entitled to Ren et al. filed on Jul. 21, 2016 and entitled "Apparatus of Plural Charged-Particle Beams", the entire disclosures of which are incorporated herein by reference.

This application is related to U.S. application Ser. No. 15/365,145 entitled to Ren et al. filed on Nov. 30, 2016 and entitled "Apparatus of Plural Charged-Particle Beams", the entire disclosures of which are incorporated herein by reference.

BACKGROUND OF THE INVENTION

1. Field of the Invention

The present invention relates to an apparatus with a plurality of charged-particle beams. More particularly, it relates to an apparatus which employs plural charged-particle beams to simultaneously acquire images of plural scanned regions within an observed area on a sample surface. Hence, the apparatus can be used to inspect and/or review defects on wafers/masks with high resolution and high throughput in semiconductor manufacturing industry.

2. Description of the Prior Art

The following description and examples are not admitted to be prior art by their mention in this Background section. For manufacturing semiconductor IC chips, pattern defects and/or uninvited particles (residuals) inevitably appear on surfaces of wafers/mask during fabrication processes, which reduce the yield to a great degree. Accordingly, the yield management tools are used to inspect and/or review the defects and the particles. To meet the more and more advanced requirements on performance of IC chips, the patterns with smaller and smaller critical feature dimensions have been adopted. Consequently, the conventional yield management tools with optical beam gradually become incompetent due to diffraction effect, and the yield management tools with electron beam are more and more employed. Compared to a photon beam, an electron beam has a shorter wavelength and thereby possibly offering superior spatial resolution. Currently, the yield management tools with electron beams employ the principle of scanning electron microscope (SEM) with a single electron beam, and as well known their throughputs are not competent for mass production. Although increasing the beam currents can improve the throughputs, the superior spatial resolutions will be fundamentally deteriorated by Coulomb Effect which increases with the beam currents.

For mitigating the limitation on throughput, instead of using a single electron beam with a large current, a promising solution is to use a plurality of electron beams each with a small current. The plurality of electron beams forms a plurality of probe spots or simply called as a probe spot array on one being-inspected or observed surface of a sample. The plurality of probe spots can respectively and simultaneously scan a plurality of small scanned regions within a large observed area on the sample surface. The electrons of each probe spot generate secondary electrons from the sample surface where they land on. The secondary electrons comprise slow secondary electrons (energies ≤50 eV) and backscattered electrons (energies close to landing energies of the electrons). The secondary electrons from the plurality of small scanned regions can be respectively and simultaneously collected by a plurality of electron detectors. Consequently, the image of the large observed area including all of the small scanned regions can be obtained much faster than scanning the large observed area with a single beam.

The plurality of electron beams can be either from a plurality of electron sources respectively, or from a single electron source. For the former, the plurality of electron beams is usually focused onto and scans the plurality of small scanned regions by a plurality of columns respectively, and the secondary electrons from each scanned region are detected by one electron detector inside the corresponding column. The apparatus therefore is generally called as a multi-column apparatus. On the sample surface, the beam interval or pitch is on the order of several to tens millimeters.

For the latter, a source-conversion unit virtually changes the single electron source into a plurality of sub-sources. The source-conversion unit comprises one beamlet-limit (or beamlet-forming) means with a plurality of beam-limit openings and one image-forming means with a plurality of electron optics elements. The plurality of beam-limit openings divides the primary-electron beam generated by the single electron source into a plurality of sub-beams or beamlets respectively, and the plurality of electron optics elements influence the plurality of beamlets to form a plurality of first parallel (virtual or real) images of the single electron source respectively. Each first image is the cross-over of one beamlet and can be taken as one sub-source which emits the corresponding beamlet. To make more beamlets available, the beamlet intervals are at micro meter level. Naturally, one primary projection imaging system and one deflection scanning unit within one single column are used to project the plurality of first parallel images onto and scan the plurality of small scanned regions respectively. The plurality of secondary electron beams therefrom is directed by one beam separator into one secondary projection imaging system, and then focused by the secondary projection imaging system to be respectively detected by a plurality of detection elements of one electron detection device inside the single column. The plurality of detection elements can be a plurality of electron detectors placed side by side or a plurality of pixels of one electron detector. The apparatus therefore is generally called as a multi-beam apparatus The beamlet-limit means is usually an electric-conduction plate with through-holes, and a plurality of through-holes therein functions the plurality of beam-limit openings respectively. For the image-forming means, each electron optics element either focuses one beamlet to form one real image (such as U.S. Pat. No. 7,244,949 and the fourth related application in the CROSS REFERENCE), or deflects one beamlet to form one virtual image (such as U.S. Pat. No. 6,943,349 and the other related applications in the CROSS REFERENCE). FIG. 1A and FIG. 1B show two examples in the fifth related application. For sake of clarity, only three beamlets are shown, and the deflection scanning unit, the beam separator, the secondary projection imaging system and the electron detection device are not shown.

In FIG. 1A, the primary-electron beam 102 generated by the electron source 101 is focused by the condenser lens 110 to be incident onto the source-conversion unit 120. The source-conversion unit 120 comprises one pre-beamlet-bending means 123 with three pre-bending micro-deflectors 123_1, 123_2 and 123_3, one beamlet-limit means 121 with three beam-limit openings 121_1, 121_2 and 121_3 and one image-forming means 122 with three electron optics elements 122_1, 122_2 and 122_3. The three pre-bending micro-deflectors 123_1~123_3 respectively deflect the three beamlets 102_1~102_3 perpendicularly incident onto the three beam-limit openings 121_1~121_3, and each of which functions as a beam-limit aperture to limit the current of the corresponding beamlet. The three electron optics elements 122_1~122_3 deflects the three beamlets 102_1~102_3 towards the primary optical axis 100_1 and form three first virtual images of the electron source 101, i.e. each beamlet has a virtual crossover. The objective lens constitutes the primary projection imaging system, which focuses the three deflected beamlets 102_1~102_3 onto the surface 7 of the sample 8, i.e. projecting the three first virtual images thereon. The three beamlets 102_1~102_3 therefore form three probe spots 102_1s, 102_2s and 102_3s on the surface 7. The currents of the probe spots 102_1s~102_3s can be varied by adjusting the focusing power of the condenser lens 110. In FIG. 1B, the movable condenser lens 210 focuses the primary-electron beam 102 to be normally incident onto the beamlet-limit means 121 of the source-conversion unit 220, and the pre-beamlet-bending means 123 in FIG. 1A is therefore not needed. Accordingly the currents of the probe spots 102_1s-102_3s can be varied by adjusting the focusing power and the position of the movable condenser lens 210. In FIG. 1A and FIG. 1B, the landing energies of the beamlets 102_1~102_3 on the sample surface 7 can be varied by adjusted either or both of the potentials of the electron source 101 and the sample surface 7.

In a multi-beam apparatus, each beamlet scans one sub-FOV (field of view) on the sample surface, and the total FOV is the sum of the sub-FOVs of the plural beamlets. Each sub-FOV is equal or smaller than the beamlet pitch on the sample surface (Ps in FIG. 1A). To further improve the throughput, each sub-FOV is better selectable in terms of the imaging resolution and the pitches of the plural beamlets are accordingly varied to keep the sub-FOVs stitched up. In one case with high image resolution, a small pixel size will be used and a small sub-FOV is desired for avoiding a large pixel number. In another case with low image resolution, a large pixel size will be used and a large sub-FOV is desired for a high throughput. FIG. 2A shows an example in the later case. As shown in dash line, if the probe spots 102_2s and 102_3s in FIG. 1A can be intentionally moved to the right and the left respectively, i.e. the pitch Ps can be changed from P1 to P2, the total FOV will be increased from 3×P1 to 3×P2, and accordingly the throughput is increased. Hence making the beamlet pitch Ps selectable will be one preferred function.

The continuous scanning mode (a sample continuously moving in the direction perpendicular to a scanning direction of a primary electron beam) is a conventional method to get high throughput in a conventional single-beam apparatus. If using this method in a multi-beam apparatus, it is better to match the orientation of the total FOV or the probe spot array with the stage moving direction. As well known, if there is one magnetic lens in the primary projection imaging system, the magnetic field thereof will rotate the plural beamlets and the total FOV as a result. Due to the magnetic field is varied with respect to the observing conditions (such as landing energies and currents of plural beamlets), the rotation angle of the total FOV will accordingly vary. FIG. 2B shows an example if the objective lens 131 in FIG. 1A is a magnetic or electromagnetic compound lens. For instance, when the landing energies of the beamlets 102_1~102_3 are changed from 1 keV to 2 keV, the probe spots 102_2s and 102_3s will rotate an angle β around the optical axis 100_1 as shown in dash line, i.e. the orientation of the total FOV rotates the angle β. The orientation variation of the total FOV impacts the performance of the continuous scanning mode. Keeping the orientation of the probe spot array same or making it selectable can provide more flexibility to improve the throughput, and accordingly is another preferred function.

For some sample, a specific match between the orientations of patterns thereon and the probe spot array may be required. Making the orientation of the probe spot array selectable can compensate the mismatch due to the limited loading accuracy, and therefore can increase the throughput by avoiding the time-consuming of re-loading. In addition, to effectively observe some patterns of a sample, the plural beamlets may be required to land onto the sample surface with specific incident angles. Making the incident angles selectable can enable more samples or patterns observable, and will be one more preferred function.

The present invention will provide methods to realize the foregoing functions in a multi-beam apparatus, especially for those proposed in the CROSS REFERENCE and used as yield management tools in semiconductor manufacturing industry.

SUMMARY OF THE INVENTION

The object of this invention is to provide a new multi-beam apparatus for observing a sample with high resolution and high throughput and in flexibly varying observing conditions. Based on the conventional multi-beam apparatuses in the CROSS REFERENCE, this invention proposes several methods to configure the new multi-beam apparatus with a variable total FOV. In the new apparatus, the total FOV can be variable in size, orientation and incident angle. Hence the new apparatus provides more flexibility to speed the sample observation and enable more kinds of samples observable. More specifically, if being used as a yield management tool in semiconductor manufacturing industry to inspect and/or review defects on wafers/masks, the new apparatus can provide more possibilities to achieve a high throughput and detect more kinds of defects.

Accordingly, the invention therefore provides a multi-beam apparatus for observing a surface of a sample, which comprises an electron source, a condenser lens below the electron source, a source-conversion unit below the condenser lens, an objective lens below the source-conversion unit, a deflection scanning unit below the source-conversion unit, a sample stage below the objective lens, a beam separator below the source-conversion unit, a secondary projection imaging system, and an electron detection device with a plurality of detection elements. The electron source, the condenser lens and the objective lens are aligned with a primary optical axis of the apparatus, and the sample stage sustains the sample so that the surface faces to the objective lens. The source-conversion unit comprises a beamlet-limit means with a plurality of beam-limit openings, and an image-forming means with a plurality of electron optics elements and movable along the primary optical axis. The electron source generates a primary-electron beam along the primary optical axis and the condenser lens focuses the primary-electron beam. A plurality of beamlets of the primary-electron beam pass through the plurality of beam-limit openings respectively, and is deflected by the plurality of electron optics elements towards the primary optical axis to form a plurality of virtual images of the electron source respectively. The plurality of beamlets is focused by the objective lens onto the surface and therefore forms a plurality of probe spots thereon respectively, and the deflection scanning unit deflects the plurality of beamlets to scan the plurality of probe spots respectively over a plurality of scanned regions within an observed area on the surface. A plurality of secondary electron beams is generated by the plurality of probe spots respectively from the plurality of scanned regions and directed into the secondary projection imaging system by the beam separator, the secondary projection imaging system focuses and keeps the plurality of secondary electron beams to be detected by the plurality of detection elements respectively, and each detection element therefore provides an image signal of one corresponding scanned region.

Deflection angles of the plurality of beamlets due to the plurality of electron optics elements are respectively set to reduce off-axis aberrations of the plurality of probe spots. Pitches of the plurality of probe spots are varied together by moving the image-forming means along the primary optical axis. The objective lens comprises a magnetic lens and an electrostatic lens. An orientation of the plurality of probe spots is selectable by varying a ratio of focusing powers of the magnetic lens and the electrostatic lens.

The deflection angles may ensure the plurality of beamlets to land on the surface perpendicularly or substantially perpendicularly. The deflection angles may ensure the plurality of beamlets to obliquely land on the surface with same or substantially same landing angles. The deflection scanning unit is above a front focal plane of the objective lens. The deflection scanning unit tilts the plurality of beamlets to obliquely land on the surface with same or substantially same landing angles. The apparatus may further comprise a beamlet-tilting deflector between the source-conversion unit and a front focal plane of the objective lens. The beamlet-tilting deflector tilts the plurality of beamlets to obliquely land on the surface with same or substantially same landing angles.

The invention also provides a multi-beam apparatus for observing a surface of a sample, which comprises an electron source, a condenser lens below the electron source, a source-conversion unit below the condenser lens, an objective lens below the source-conversion unit, a deflection scanning unit below the source-conversion unit, a sample stage below the objective lens, a beam separator below the source-conversion unit, a secondary projection imaging system, and an electron detection device with a plurality of detection elements. The electron source, the condenser lens and the objective lens are aligned with a primary optical axis of the apparatus, and the sample stage sustains the sample so that the surface faces to the objective lens. The source-conversion unit comprises a beamlet-limit means with a plurality of beam-limit openings, a first image-forming means with a plurality of first electron optics elements and a second image-forming means with a plurality of second electron optics elements, the second image-forming means is below the first image-forming means and movable in a radial direction, and one of the first image-forming means and the second image-forming means is used as an active image-forming means. The electron source generates a primary-electron beam along the primary optical axis and the condenser lens focuses the primary-electron beam. A plurality of beamlets of the primary-electron beam pass through the plurality of beam-limit openings respectively, and is deflected by the active image-forming means towards the primary optical axis to form a plurality of virtual images of the electron source respectively. The plurality of beamlets is focused by the objective lens onto the surface and therefore forms a plurality of probe spots thereon respectively, and the deflection scanning unit deflects the plurality of beamlets to scan the plurality of probe spots respectively over a plurality of scanned regions within an observed area on the surface. A plurality of secondary electron beams is generated by the plurality of probe spots respectively from the plurality of scanned regions and directed into the secondary projection imaging system by the beam separator, the secondary projection imaging system focuses and keeps the plurality of secondary electron beams to be detected by the plurality of detection elements respectively, and each detection element therefore provides an image signal of one corresponding scanned region.

Deflection angles of the plurality of beamlets due to the active image-forming means are respectively set to reduce off-axis aberrations of the plurality of probe spots. Pitches of the plurality of probe spots are varied together by changing the active image-forming means between the first image-forming means and the second image-forming means, and when the first image-forming means is selected, the second image-forming means is moved outside so as not to block the plurality of beamlets. The objective lens comprises a magnetic lens and an electrostatic lens. An orientation of the plurality of probe spots is selectable by varying a ratio of focusing powers of the magnetic lens and the electrostatic lens.

The deflection angles may ensure the plurality of beamlets to land on the surface perpendicularly or substantially perpendicularly. The deflection angles may ensure the plurality of beamlets to obliquely land on the surface with same or substantially same landing angles. The deflection scanning unit is above a front focal plane of the objective lens. The deflection scanning unit tilts the plurality of beamlets to obliquely land on the surface with same or substantially same landing angles. The apparatus may further comprise a beamlet-tilting deflector between the source-conversion unit and a front focal plane of the objective lens. The beamlet-tilting deflector tilts the plurality of beamlets to obliquely land on the surface with same or substantially same landing angles.

The invention also provides a multi-beam apparatus for observing a surface of a sample, which comprises an electron source, a condenser lens below the electron source, a source-conversion unit below the condenser lens, an objective lens below the source-conversion unit, a deflection scanning unit below the source-conversion unit, a sample stage below the objective lens, a beam separator below the source-conversion unit, a secondary projection imaging system, and an electron detection device with a plurality of detection elements. The electron source, the condenser lens and the objective lens are aligned with a primary optical axis of the apparatus, a first principal plane of the objective lens is movable along the primary optical axis, and the sample stage sustains the sample so that the surface faces to the objective lens. The source-conversion unit comprises a beamlet-limit means with a plurality of beam-limit openings, and an image-forming means with a plurality of electron optics elements. The electron source generates a primary-electron beam along the primary optical axis and the condenser lens focuses the primary-electron beam. A plurality of beamlets of the primary-electron beam pass through the plurality of beam-limit openings respectively, and is deflected by the plurality of electron optics elements towards the primary optical axis to form a plurality of virtual images of the electron source respectively. The plurality of beamlets is focused by the objective lens onto the surface and therefore forms a plurality of probe spots thereon respectively, and the deflection scanning unit deflects the plurality of beamlets to scan the plurality of probe spots respectively over a plurality of scanned regions within an observed area on the surface. A plurality of secondary electron beams is generated by the plurality of probe spots respectively from the plurality of scanned regions and directed into the secondary projection imaging system by the beam separator, the secondary projection imaging system focuses and keeps the plurality of secondary electron beams to be detected by the plurality of detection elements respectively, and each detection element therefore provides an image signal of one corresponding scanned region.

Deflection angles of the plurality of beamlets due to the plurality of electron optics elements are respectively set to reduce off-axis aberrations of the plurality of probe spots. Pitches of the plurality of probe spots are varied together by moving the first principal plane along the primary optical axis.

The deflection angles may ensure the plurality of beamlets to land on the surface perpendicularly or substantially perpendicularly. The deflection angles may ensure the plurality of beamlets to obliquely land on the surface with same or substantially same landing angles. The deflection scanning unit is above a front focal plane of the objective lens. The deflection scanning unit tilts the plurality of beamlets to obliquely land on the surface with same or substantially same landing angles. The apparatus may further comprise a beamlet-tilting deflector between the source-conversion unit and a front focal plane of the objective lens. The beamlet-tilting deflector tilts the plurality of beamlets to obliquely land on the surface with same or substantially same landing angles. The objective lens comprises a lower magnetic lens and an electrostatic lens. The electrostatic lens comprises a field-control electrode and a field-moving electrode, and generates an electrostatic field. A potential of the field-control electrode is set to control the electrostatic field on the surface for the sample free of electrical breakdown. A potential of the field-moving electrode is set to move the electrostatic field for moving the first principal plane. An orientation of the plurality of probe spots is selectable by varying either or both of potentials of the field-control electrode and the field-moving electrode. The apparatus may further comprise an upper magnetic lens above the lower magnetic lens. The first principal plane is moved by varying a ratio of focusing powers of the lower magnetic lens and the upper magnetic lens. An orientation of the plurality of probe spots is selectable by setting polarities of magnetic fields of the upper and lower magnetic lenses same or opposite.

The invention also provides a multi-beam apparatus for observing a surface of a sample, which comprises an electron source, a condenser lens below the electron source, a source-conversion unit below the condenser lens, a transfer lens below the source-conversion unit, a field lens below the transfer lens, an objective lens below the field lens, a deflection scanning unit below the source-conversion unit, a sample stage below the objective lens, a beam separator below the source-conversion unit, a secondary projection imaging system, and an electron detection device with a plurality of detection elements. The electron source, the condenser lens, the transfer lens, the field lens and the objective lens are aligned with a primary optical axis of the apparatus, and the sample stage sustains the sample so that the surface faces to the objective lens. The source-conversion unit comprises a beamlet-limit means with a plurality of beam-limit openings, and an image-forming means with a plurality of electron optics elements. The electron source generates a primary-electron beam along the primary optical axis and the condenser lens focuses the primary-electron beam. A plurality of beamlets of the primary-electron beam pass through the plurality of beam-limit openings respectively, and is deflected by the plurality of electron optics elements towards the primary optical axis to form a plurality of first virtual images of the electron source respectively. The transfer lens images the plurality of first virtual images onto an intermediate image plane and therefore forms a plurality of second real images respectively thereon, the field lens is placed on the intermediate image plane and bends the plurality of beamlets, the objective lens images the plurality of second real images onto the surface and therefore forms a plurality of probe spots thereon respectively, and the deflection scanning unit deflects the plurality of beamlets to scan the plurality of probe spots respectively over a plurality of scanned regions within an observed area on the surface. A plurality of secondary electron beams is generated by the plurality of probe spots respectively from the plurality of scanned regions and directed into the secondary projection imaging system by the beam separator, the secondary projection imaging system focuses and keeps the plurality of secondary electron beams to be detected by the plurality of detection elements respectively, and each detection element therefore provides an image signal of one corresponding scanned region.

Bending angles of the plurality of beamlets due to the field lens are set to reduce off-axis aberrations of the plurality of probe spots. Deflection angles of the plurality of beamlets due to the plurality of electron optics elements are adjusted to change pitches of the plurality of probe spots respectively. The objective lens comprises a first magnetic lens and a first electrostatic lens. An orientation of the plurality of probe spots is selectable by varying a ratio of focusing powers of the first magnetic lens and the first electrostatic lens. The transfer lens comprises a second magnetic lens and a second electrostatic lens. An orientation of the plurality of probe spots is selectable by varying a ratio of focusing powers of the second magnetic lens and the second electrostatic lens. The field lens comprises a third magnetic lens and a third electrostatic lens. An orientation of the plurality of probe spots is selectable by varying a ratio of focusing powers of the third magnetic lens and the third electrostatic lens. The bending angles and deflection angles of the plurality of beamlets due to the plurality of electron optics elements may ensure the plurality of beamlets to land on the surface perpendicularly or substantially perpendicularly. The bending angles and deflection angles of the plurality of beamlets due to the plurality of electron optics elements may ensure the plurality of beamlets to obliquely land on the surface with same or substantially same landing angles. The deflection scanning unit is above a front focal plane of the objective lens. The deflection scanning unit tilts the plurality of beamlets to obliquely land on the surface with same or substantially same landing angles. The apparatus may further comprise a beamlet-tilting deflector between the source-conversion unit and a front focal plane of the objective lens. The beamlet-tilting deflector tilts the plurality of beamlets to obliquely land on the surface with same or substantially same landing angles.

The invention also provides a method to configure a multi-beam apparatus for observing a surface of a sample, which comprises steps of configuring an image-forming means of a source-conversion unit movable along a primary optical axis thereof; using the image-forming means to form a plurality of virtual images of an electron source respectively; using an objective lens to image the plurality of virtual images onto the surface and form a plurality of probe spots thereon; and moving the image-forming means to vary pitches of the plurality of probe spots.

The invention also provides a method to configure a multi-beam apparatus for observing a surface of a sample, which comprises steps of configuring a source-conversion unit with a first image-forming means and a second image-forming means, wherein the second image-forming means is farther away from an electron source than the first image-forming means and movable in a radial direction of the apparatus; using one of the first image-forming means and the second image-forming means as an active image-forming means, wherein when the first image-forming means is used, the second image-forming means is moved away; using the active image-forming means to form a plurality of virtual images of the electron source respectively; using an objective lens to image the plurality of virtual images onto the surface and form a plurality of probe spots thereon; and changing the active image-forming means between the first image-forming means and the second image-forming means to vary pitches of the plurality of probe spots.

The invention also provides a method to configure a multi-beam apparatus for observing a surface of a sample, which comprises steps of configuring an objective lens with a first principal plane movable along a primary optical axis of the apparatus; using an image-forming means of a source-conversion unit to form a plurality of virtual images of an electron source respectively; using the objective lens to image the plurality of virtual images onto the surface and form a plurality of probe spots thereon; and moving the first principal plane to vary pitches of the plurality of probe spots.

The invention also provides a method to configure a multi-beam apparatus for observing a surface of a sample, which comprises steps of configuring an objective lens with a lower magnetic lens and an electrostatic lens in the apparatus; using an image-forming means of a source-conversion unit to form a plurality of virtual images of an electron source respectively; using the objective lens to image the plurality of virtual images onto the surface and form a plurality of probe spots thereon; and changing a ratio of focusing powers of the magnetic lens and the electrostatic lens to select an orientation of the plurality of probe spots.

The method may further comprise a step of configuring the objective lens with an upper magnetic lens farther away from the surface than the lower magnetic lens. The method may further comprise a step of changing polarities of magnetic fields of the upper and lower magnetic lenses to select the orientation.

The invention also provides a method to configure a multi-beam apparatus for observing a surface of a sample, which comprises steps of using an image-forming means of a source-conversion unit to deflect a plurality of beamlets from an electron source to form a plurality of first virtual images thereof respectively; using an objective lens to image the plurality of virtual images onto the surface and form a plurality of probe spots thereon; and setting deflection angles of the plurality of beamlets due to the image-forming means so that the plurality of beamlets lands on the surface with same or substantially same landing angles.

The method may further comprise a step of changing the deflection angles to equally vary the landing angles. The method may further comprise a step of using a deflection scanning unit to tilt the plurality of beamlets so as to equally vary the landing angles. The method may further comprise a step of using a beamlet-tilting deflector to tilt the plurality of beamlets so as to equally vary the landing angles.

The invention also provides a method to configure a multi-beam apparatus for observing a surface of a sample, which comprises steps of using an image-forming means of a source-conversion unit to deflect a plurality of beamlets from an electron source to form a plurality of first virtual images thereof respectively; using a transfer lens to image the plurality of first virtual images onto an intermediate image plane and forms a plurality of second real images respectively; placing a field lens on the intermediate image plane to bend the plurality of beamlets; and using an objective lens to image the plurality of second real images onto the surface and form a plurality of probe spots thereon.

The method may further comprise a step of changing deflection angles of the plurality of beamlets due to the image-forming means to vary pitches of the plurality of probe spots. The method may further comprise a step of setting deflection angles of the plurality of beamlets due to the image-forming means and bending angles of the plurality of beamlets due to the field lens so that the plurality of beamlets lands on the surface with same or substantially same landing angles. The method may further comprise a step of varying the deflection angles to equally change the landing angles. The method may further comprise a step of using a deflection scanning unit to tilt the plurality of beamlets to equally change the landing angles. The method may further comprise a step of using a beamlet-tilting deflector to tilt the plurality of beamlets to equally change the landing angles. The method may further comprise a step of configuring the objective lens with a first magnetic lens and a first electrostatic lens. The method may further comprise a step of changing a ratio of focusing powers of the first magnetic lens and the first electrostatic lens to select an orientation of the plurality of probe spots. The method may further comprise a step of configuring the transfer lens with a second magnetic lens and a second electrostatic lens. The method may further comprise a step of changing a ratio of focusing powers of the second magnetic lens and the second electrostatic lens to select an orientation of the plurality of probe spots. The method may further comprise a step of configuring the field lens with a third magnetic lens and a third electrostatic lens. The method may further comprise a step of changing a ratio of focusing powers of the third magnetic lens and the third electrostatic lens to select an orientation of the plurality of probe spots.

The invention also provides an apparatus, which comprises a source for providing a primary charged particle beam, a source-conversion unit for dividing the primary charged particle beam into a plurality of charged particle beamlets and using which to form a plurality of images of the source respectively, and an objective lens below the source-conversion unit for projecting the plurality of images onto a sample surface. Pitches of the plurality of charged particle beamlets on the sample surface are adjustable by changing deflection angles of the plurality of charged particle beamlets prior entering the objective lens.

The invention also provides an apparatus, which comprises a source for providing a primary charged particle beam, means for using a plurality of beamlets of the primary charged particle beam to form a plurality of images of the source, an objective lens for projecting the plurality of images onto a sample surface to form a plurality of probe spots, and means for adjusting pitches of the plurality of probe spots on the sample surface.

The invention also provides a method for observing a sample surface, which comprises steps of providing a plurality of charged particle beams with a plurality of crossovers respectively, projecting the plurality of crossovers onto the sample surface to form a plurality of probe spots thereon, scanning the plurality of probe spots on the sample surface, and changing deflection angles of the plurality of charged particle beams such that pitches of the plurality of spots can be adjusted.

Other advantages of the present invention will become apparent from the following description taken in conjunction with the accompanying drawings wherein are set forth, by way of illustration and example, certain embodiments of the present invention.

BRIEF DESCRIPTION OF THE DRAWINGS

The present invention will be readily understood by the following detailed description in conjunction with the accompanying drawings, wherein like reference numerals designate like structural elements, and in which:

FIGS. 1A and 1B are schematic illustrations of two configurations of the conventional multi-beam apparatus disclosed in the fifth application of the CROSS REFERENCE.

FIG. 1C is a schematic illustration of one configuration of a conventional electromagnetic compound objective lens.

DETAILED DESCRIPTION OF EXAMPLE EMBODIMENTS

Figure 2A:
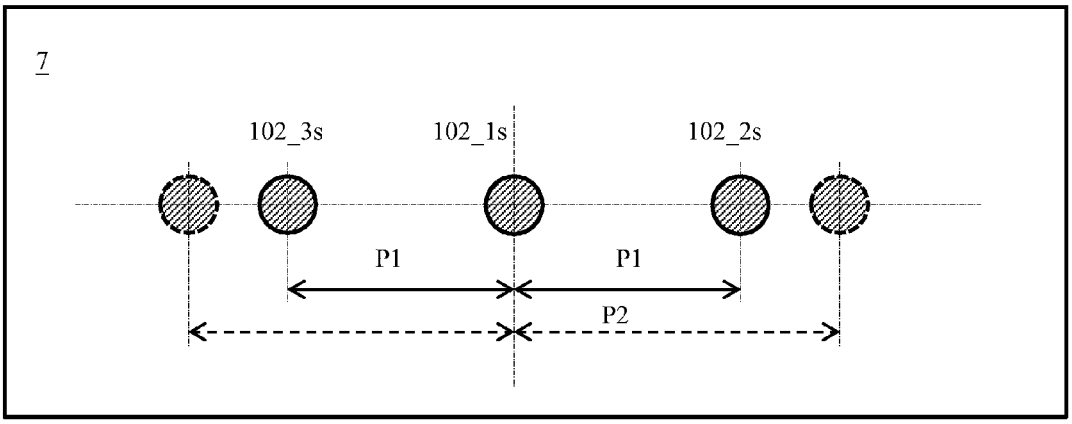
FIGS. 2A and 2B are schematic illustrations of the total FOV varying in size and orientation.
Figure 2B:
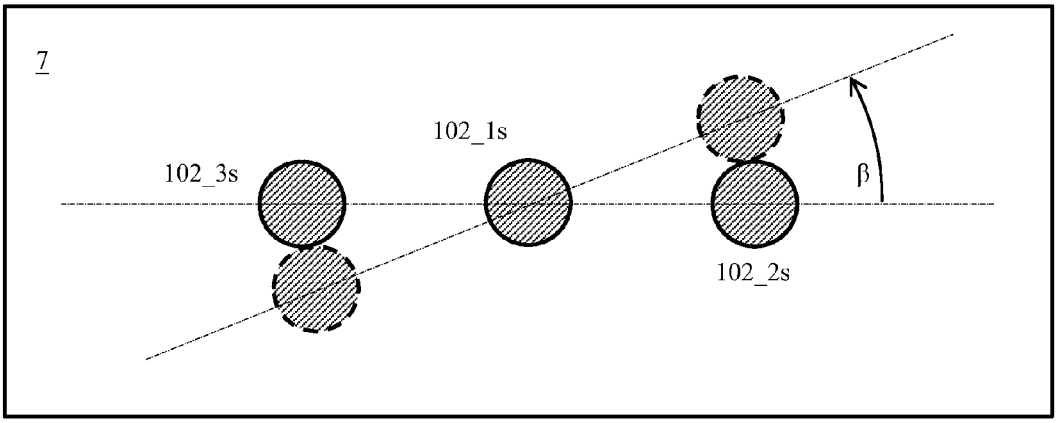

Various example embodiments of the present invention will now be described more fully with reference to the accompanying drawings in which some example embodiments of the invention are shown. Without limiting the scope of the protection of the present invention, all the description and drawings of the embodiments will exemplarily be referred to an electron beam. However, the embodiments are not used to limit the present invention to specific charged particles.

In the drawings, relative dimensions of each component and among every component may be exaggerated for clarity. Within the following description of the drawings, the same or like reference numbers refer to the same or like components or entities, and only the differences with respect to the individual embodiments are described.

Accordingly, while example embodiments of the invention are capable of various modifications and alternative forms, embodiments thereof are shown by way of example in the drawings and will herein be described in detail. It should be understood, however, that there is no intent to limit example embodiments of the invention to the particular forms disclosed, but on the contrary, example embodiments of the invention are to cover all modifications, equivalents, and alternatives falling within the scope of the invention.

In this invention, "axial" means "in the optical axis direction of an electron optics element (such as a round lens or a multipole lens), or an imaging system or an apparatus", "radial" means "in a direction perpendicular to the optical axis", "on-axial" means "on or aligned with the optical axis, and "off-axis" means "not on or aligned with the optical axis".

In this invention, "an imaging system is aligned with an optical axis" means "all the electron optics elements (such round lens and multipole lens) are aligned with the optical axis".

In this invention, X, Y and Z axe form Cartesian coordinate. The optical axis of the primary projection imaging system is on the Z-axis, and the primary electron beam travels along the Z-axis.

In this invention, "primary electrons" means "electrons emitted from an electron source and incident onto a being-observed or inspected surface of a sample, and "secondary electrons" means "electrons generated from the surface by the "primary electrons".

In this invention, "pitch" means an interval between two adjacent beamlets or beams on a plane.

In this invention, "effective deflection plane of a deflector" means "the plane where the total deflection function of the deflector can be equivalent to happen".

Based on some conventional multi-beam apparatuses proposed in the CROSS REFERENCE, this invention proposes several methods to configure a new multi-beam apparatus with a variable total FOV. In the new apparatus, the total FOV can be variable in size, orientation and illumination angle. To clearly express the methods, the multi-beam apparatus in FIG. 1B is taken as an example. For sake of simplification in explanation, in the new apparatus, only three beamlets are shown but the number of beamlets can be anyone. In addition, one of the three beamlets is on-axis, but they can all be off-axis. In addition, the elements not related to the methods, such as the deflection scanning unit and the beam separator, are not shown or even not mentioned in the illustrations and the description of the embodiments.

In each of those conventional multi-beam apparatuses, the plural beamlets are deflected towards the optical axis by the image-forming means. The deflection angles of the plural beamlets are set to minimize the off-axis aberrations of the plural probe spots due to the objective lens. Accordingly the plural deflected beamlets typically pass through or approach the front focal point of the objective lens, i.e. forming an on-axis crossover on or close to the front focal plane of the objective lens. The pitches of the plural probe spots therefore depend on the deflection angles of the plural beamlets and the first (or object) focal length of the objective lens. Hence the pitches can be varied by changing the deflection angles and/or the first focal length of the objective lens. For example, in FIG. 1A or FIG. 1B, the deflection angles $\alpha_2$ and $\alpha_3$ of the two off-axis beamlets 102_2 and 102_3 are set to minimize the off-axis aberrations of the probe spots 102_2s and 102_3s due to the objective lens 131. Accordingly the beamlets 102_2 and 102_3 typically pass through or approach the front focal point of the objective lens 131, i.e. forming the crossover CV on the optical axis and on or close to the front focal plane of the objective lens 131. The pitch Ps between the probe spots 102_1s and 102_2s is determined by the deflection angle $\alpha 2$ and the first focal length f of the objective lens 131, and can be simply expressed as $Ps \approx \alpha_2 \cdot f$. Similarly, the pitch Ps between the probe spots 102_1s and 102_3s can be simply expressed as $Ps \approx \alpha_3 \cdot f$.

Figure 3A:
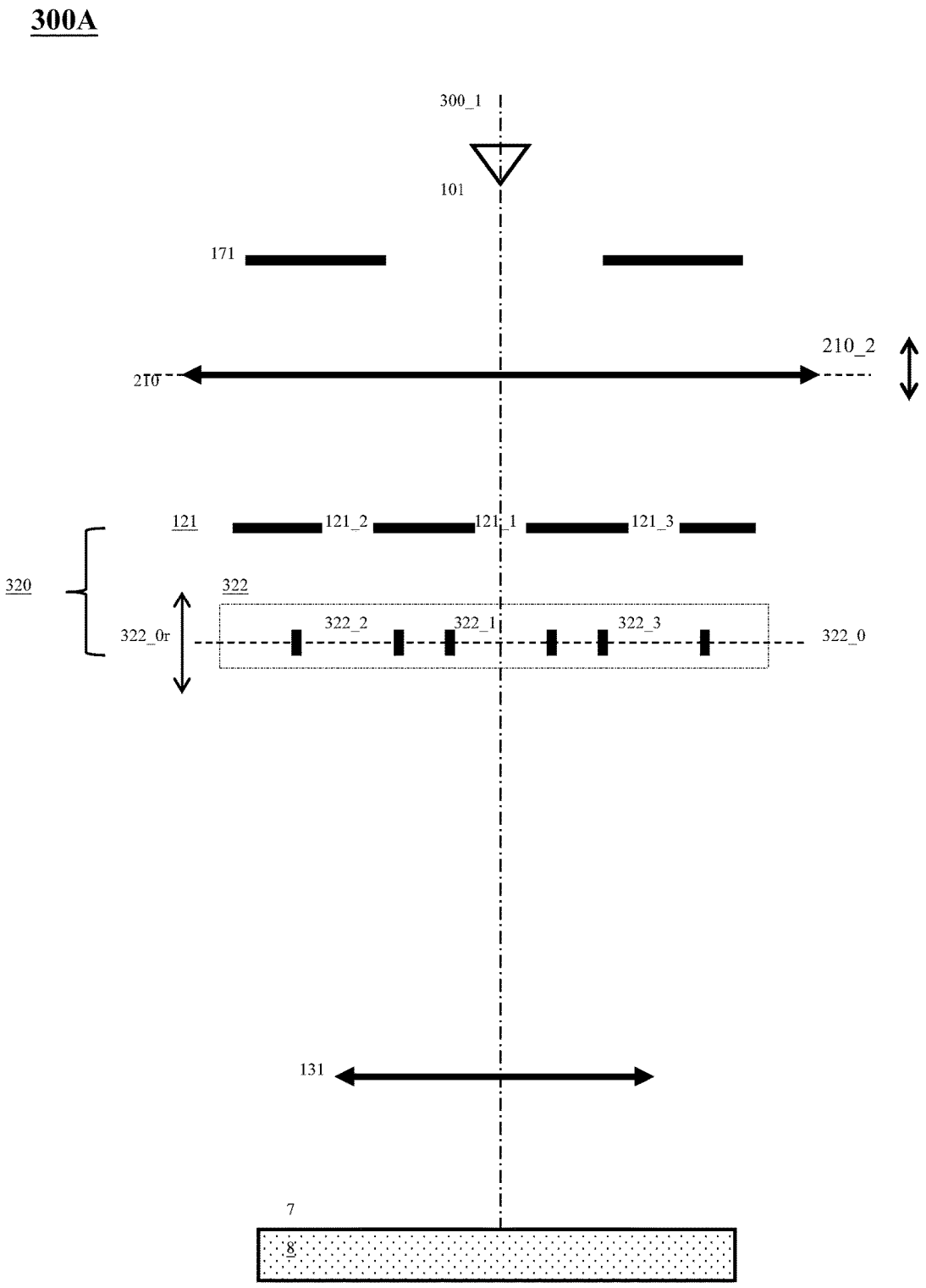
FIG. 3A is a schematic illustration of one configuration of the new multi-beam apparatus in accordance with one embodiment of the present invention.
Figure 4A:
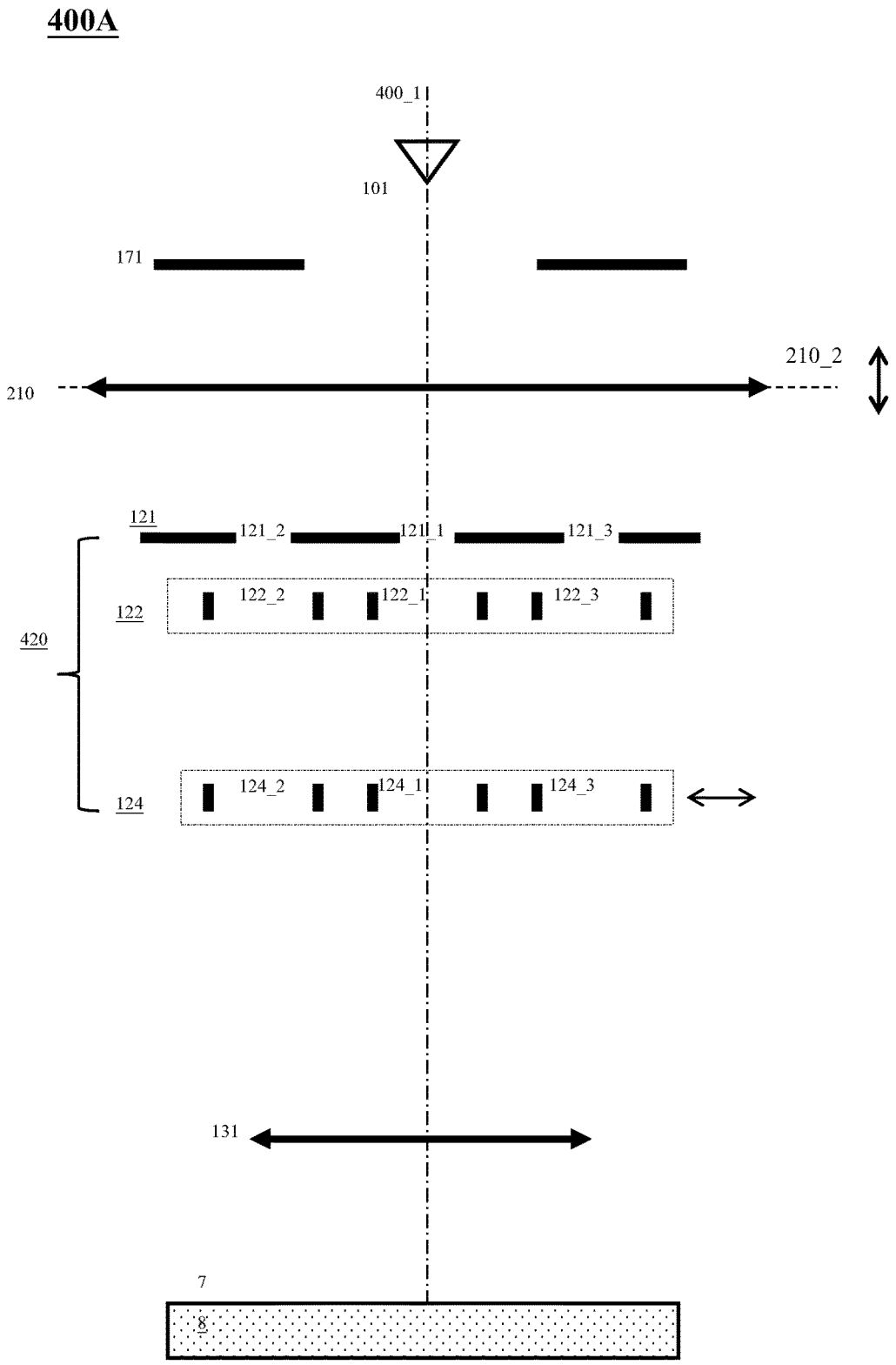
FIG. 4A is a schematic illustration of another configuration of the new multi-beam apparatus in accordance with another embodiment of the present invention.
Figure 5A:
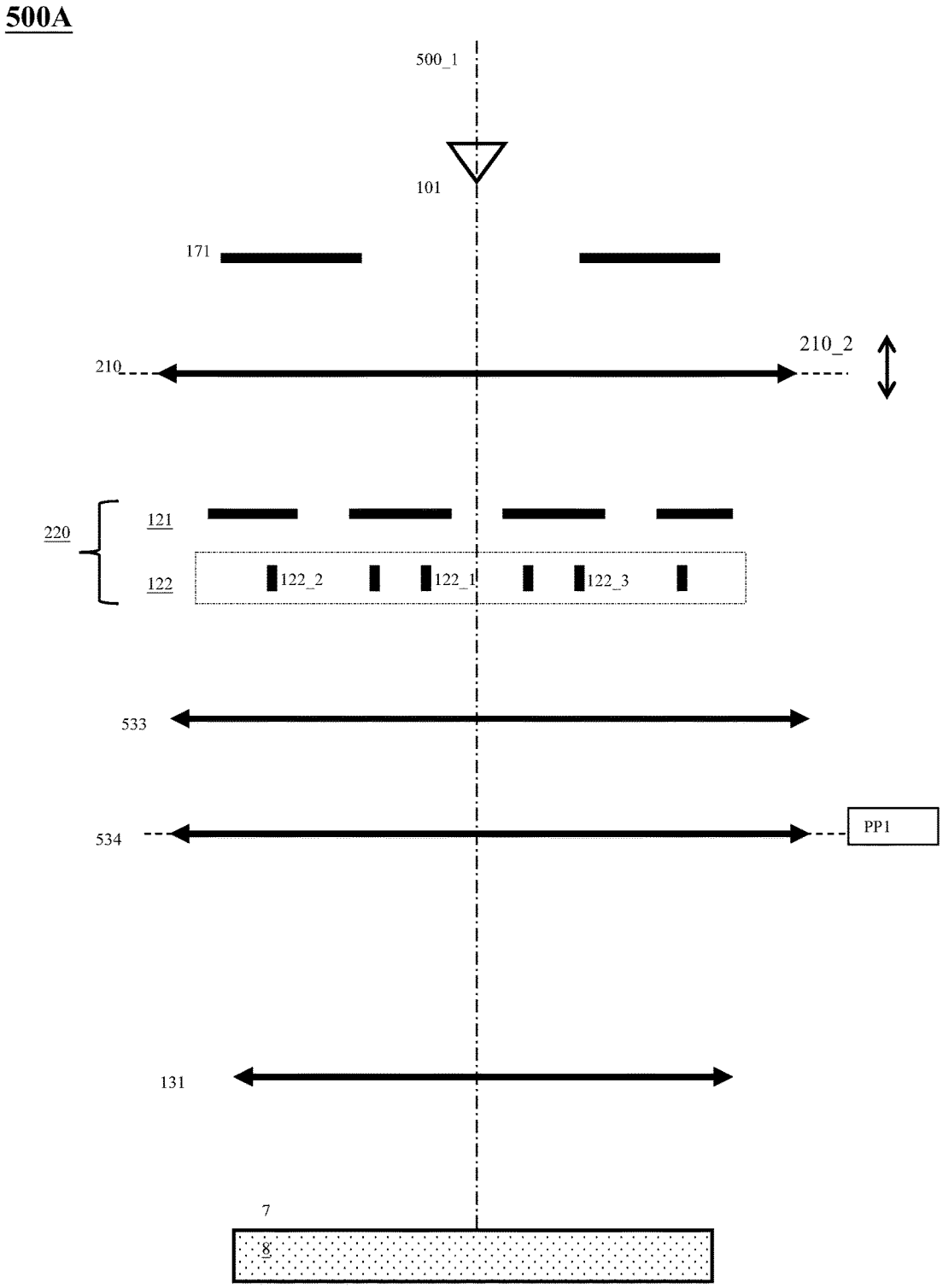
FIG. 5A is a schematic illustration of another configuration of the new multi-beam apparatus in accordance with another embodiment of the present invention.
Figure 6A:
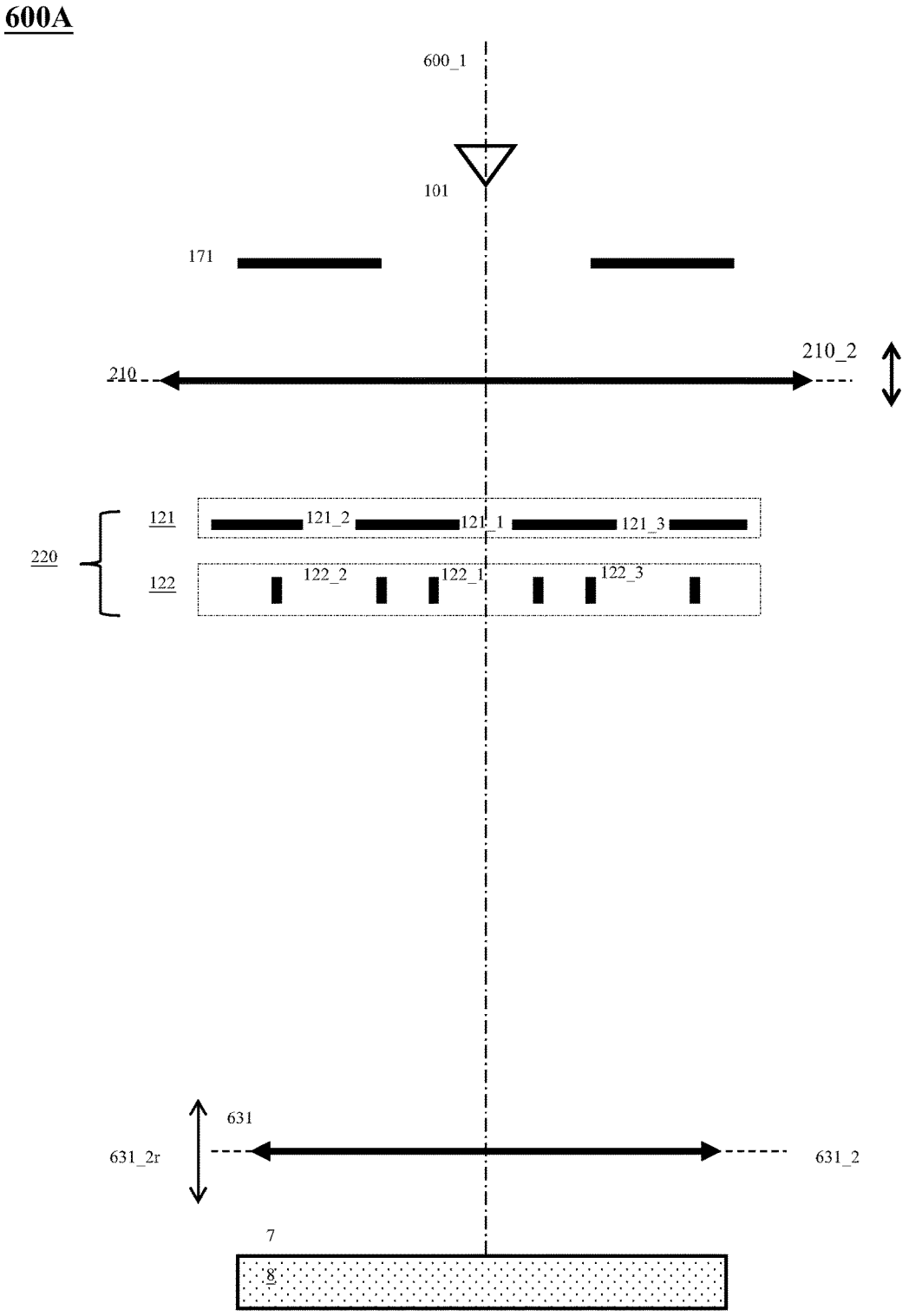
FIG. 6A is a schematic illustration of another configuration of the new multi-beam apparatus in accordance with another embodiment of the present invention.

FIG. 3A, FIG. 4A and FIG. 5A show three embodiments 300A, 400A and 500A of the new apparatus changing the pitches by varying the deflection angles, and FIG. 6A shows one embodiment 600A changing the pitches by varying the first focal length. In the embodiment 300A, the source-conversion unit 320 comprises one beamlet-limit means 121 with three beam-limit opening 121_1, 121_2 and 121_3, and one movable image-forming means 322 with three electron optics elements 322_1, 322_2 and 322_3. The effective deflection plane 322_0 of the movable image-forming means 322 can be moved along the optical axis 300_1 within the variation range 322_0r. The pitches of the plural probe spots will become large as the effective deflection plane 322_0 is moved close to the objective 131 and vice versa.

Figure 3B:
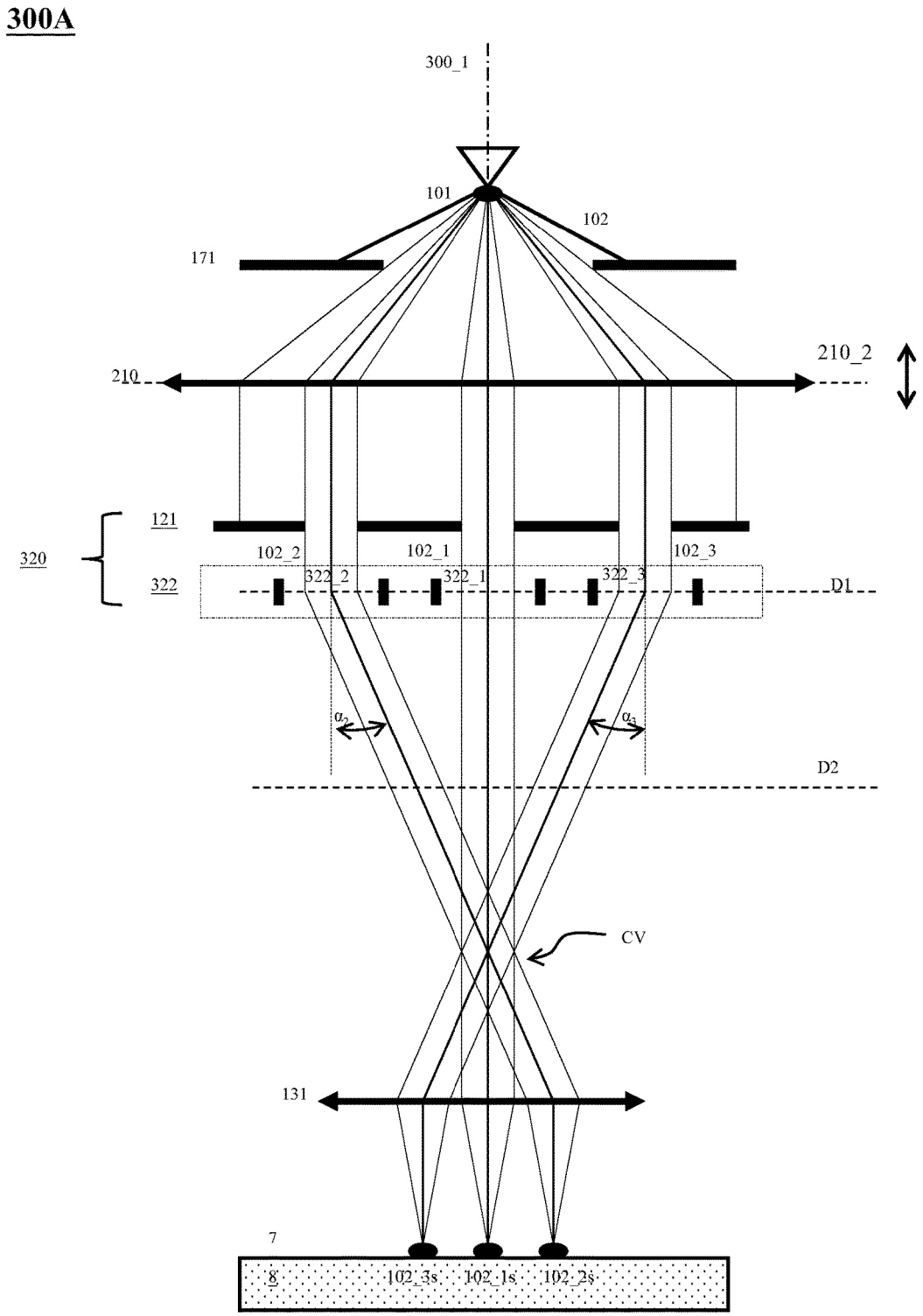
FIGS. 3B and 3C are schematic illustrations of varying the size of the total FOV in accordance with the embodiment in FIG. 3A.
Figure 3C:
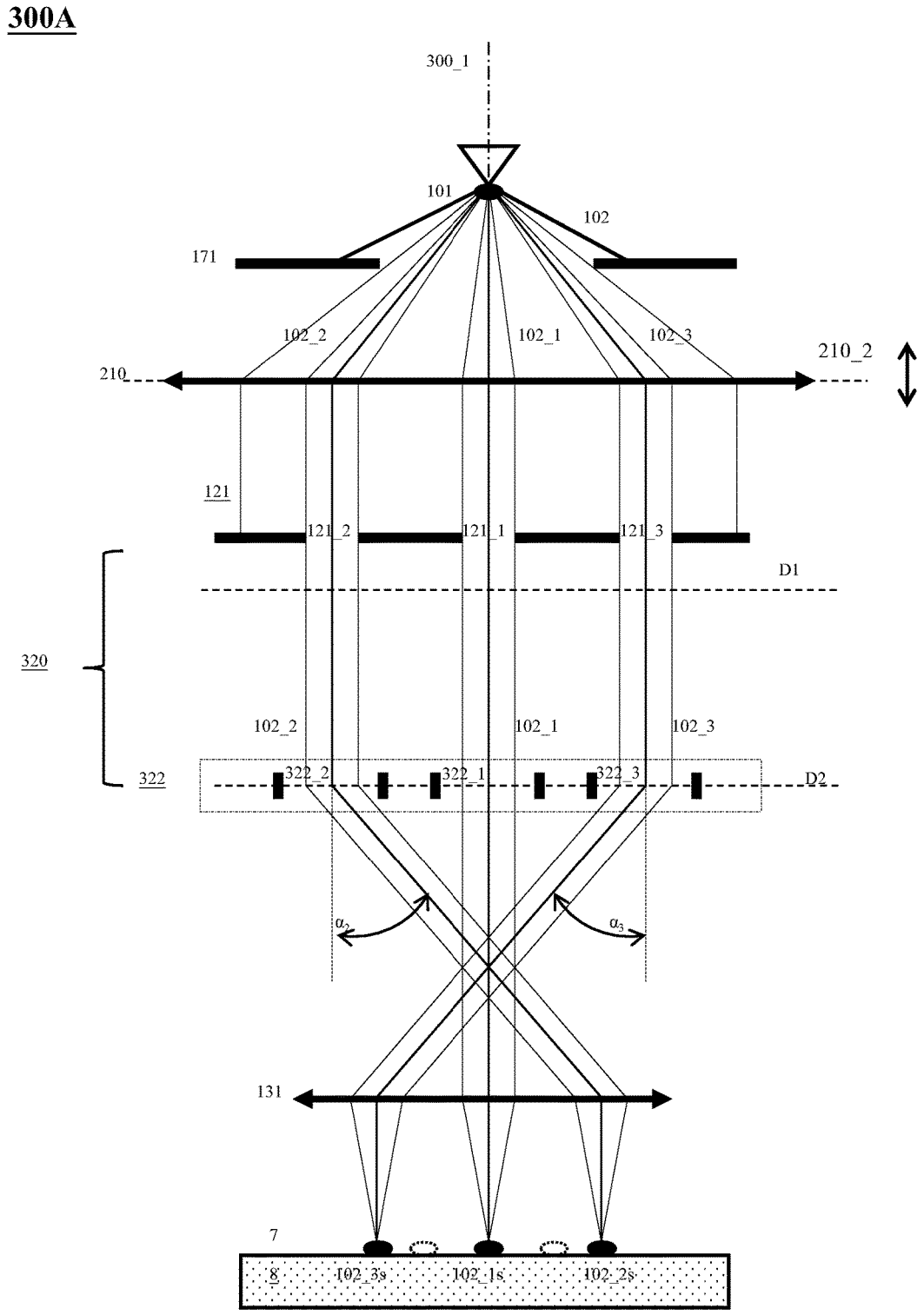

FIG. 3B shows the paths of three beamlets 102_1, 102_2 and 102_3 when the effective deflection plane 322_0 is on the position D1. The movable condenser lens 210 collimates the primary electron beam 102 to be normally incident onto the source-conversion unit 320. The beam-limit openings 121_1~121_3 divide the primary electron beam 102 into one on-axis beamlet 102_1, and two off-axis beamlets 102_2 and 102_3. The two off-axis electron optics elements 322_2 and 322_3 deflect the beamlets 102_2 and 102_3 respectively towards the optical axis 300_1. The three beamlets 102_1~102_3 are focused onto the sample surface 7 by the objective lens 131 and therefore form three probe spots 102_1s, 102_2s and 102_3s respectively. The deflection angles $\alpha_2$ and $\alpha_3$ of the beamlets 102_2 and 102_3 are set to minimize the off-axis aberrations of the probe spots 102_2s and 102_3s. Accordingly the beamlets 102_2 and 102_3 pass through or approach the front focal point of the objective lens 131, i.e. forming a crossover on the optical axis 300_1 and on or close to the front focal plane thereof. The two pitches formed by the probe spots 102_1s~102_3s are approximately equal to $\alpha_2 \cdot f$ and $\alpha_3 \cdot f$ respectively. The f is the first focal length of the objective lens 131. The effective deflection plane 322_0 in FIG. 3C is on the position D2 closer to the objective 131 than the position D1. Accordingly, the deflection angles $\alpha_2$ and $\alpha_3$ are increased and the two pitches become larger. The probe spots 102_2s and 102_3s move outside from the previous positions (dash line) in FIG. 3B.

Figure 4B:
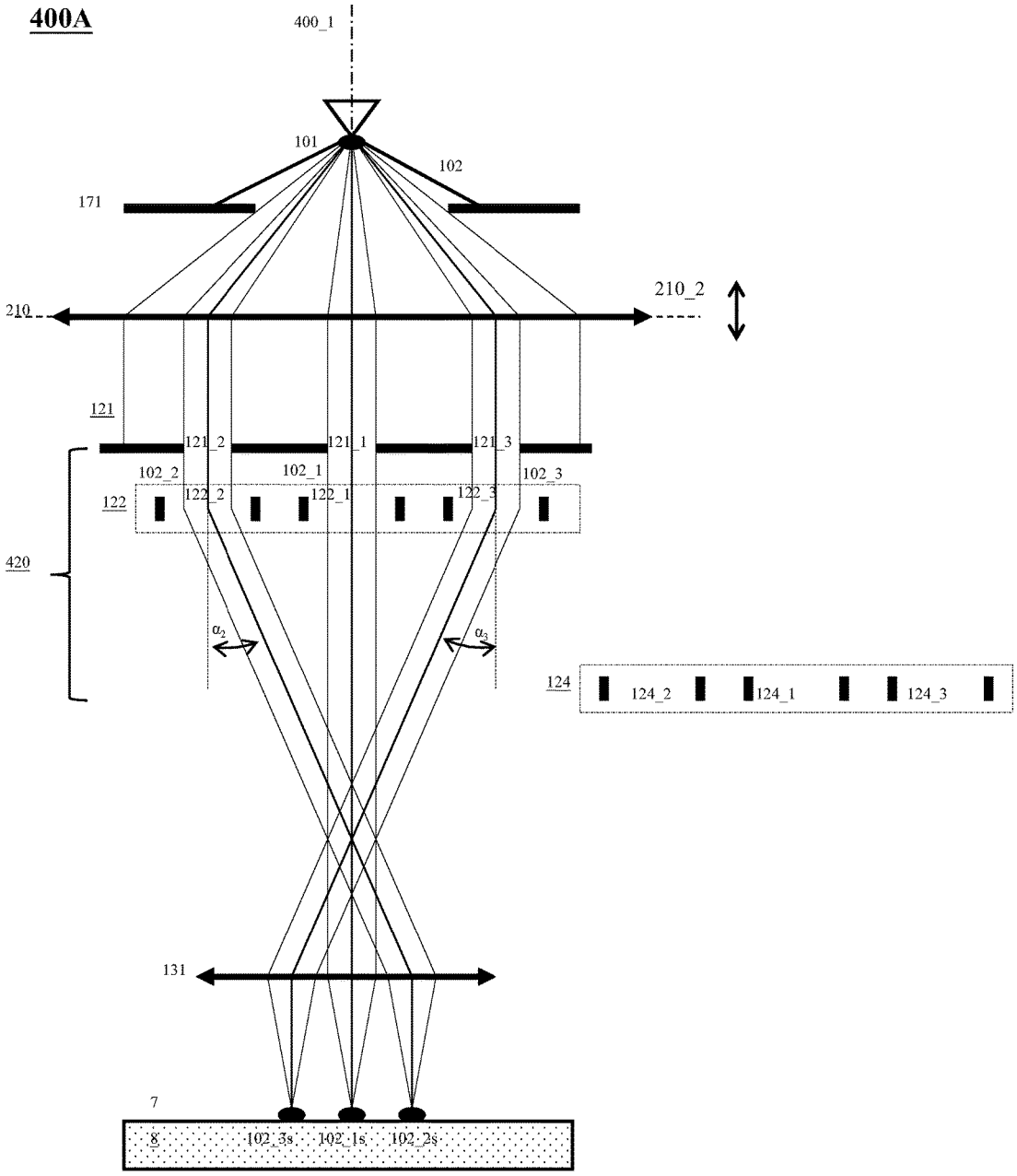
FIGS. 4B and 4C are schematic illustrations of varying the size of the total FOV in accordance with the embodiment in FIG. 4A.
Figure 4C:
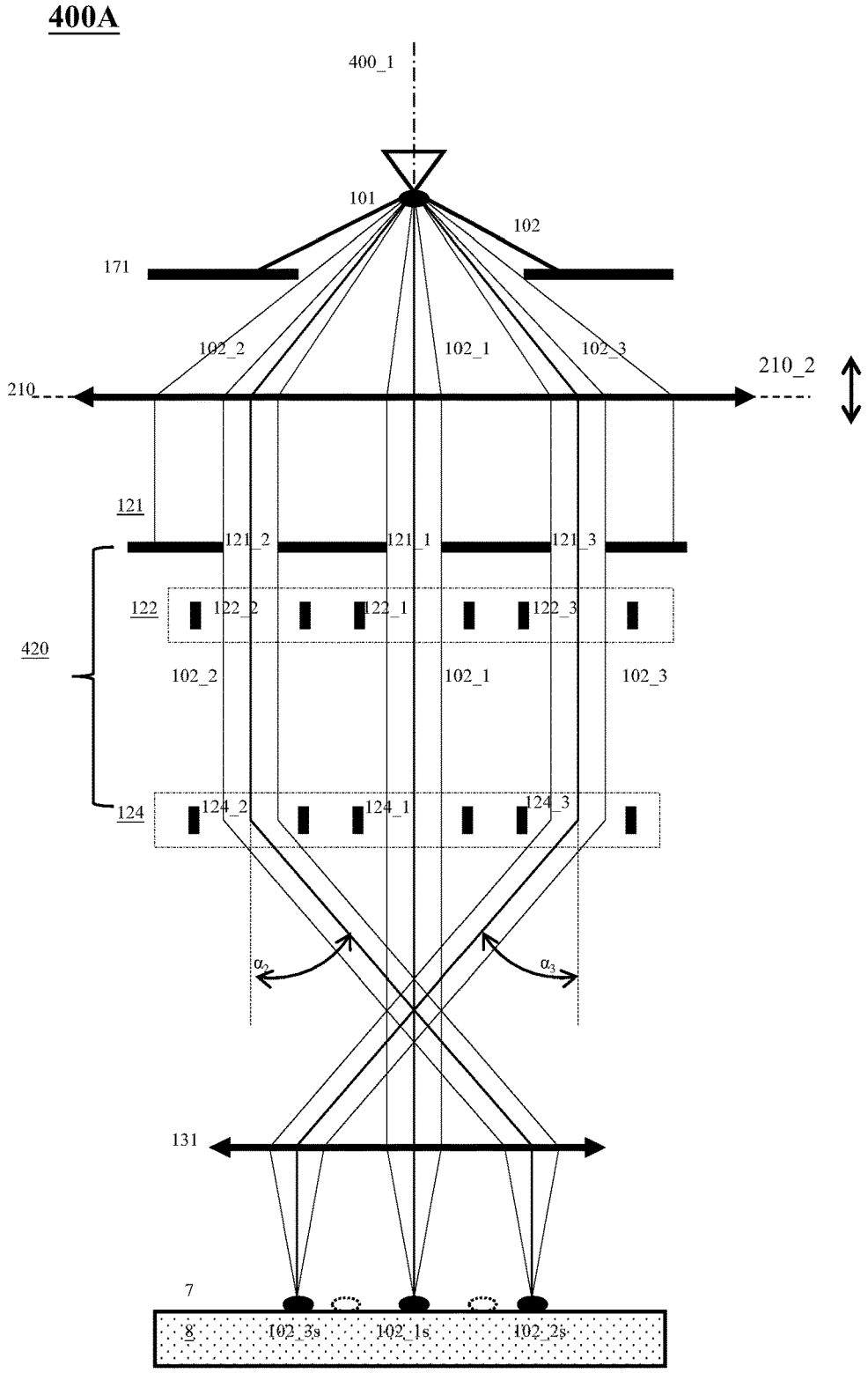

In the embodiment 400A in FIG. 4A, the source-conversion unit 420 comprises one more image-forming means 124 in comparison with FIG. 1B. The image-forming means 124 with three electron optics elements 124_1, 124_2 and 124_3 is below the imaging-forming means 122, and can be moved in a radial direction. Accordingly the source-conversion unit 420 works in two modes. In the first mode as shown in FIG. 4B, the image-forming means 122 is used to form three first virtual images of the single electron source 101, and the image-forming means 124 is moved outside the path of the beamlets 102_1~102_3. In the second mode as shown in FIG. 4C, the image-forming means 122 is switched off, and the image-forming means 124 is moved back to form three first virtual images of the single electron source 101. The deflection angles $\alpha_2$ and $\alpha_3$ of the beamlets 102_2 and 102_3 are smaller in the first mode than in the second mode, and accordingly the two pitches are larger in the second mode. In FIG. 4C, the probe spots 102_2s and 102_3s move outside from the previous positions (dash line) in FIG. 4B.

Figure 5B:
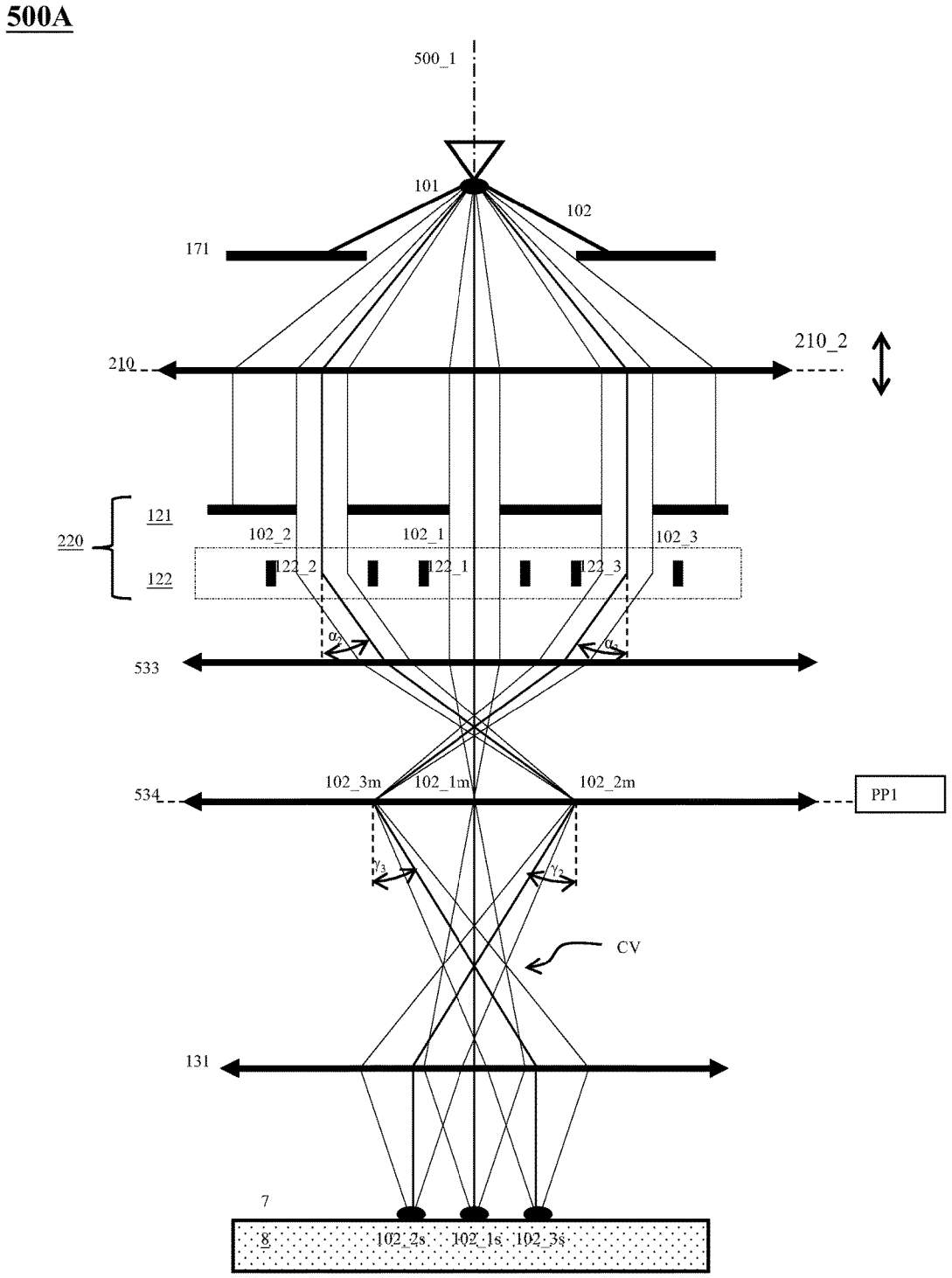
FIGS. 5B and 5C are schematic illustrations of varying the size of the total FOV in accordance with the embodiment in FIG. 5A.

The embodiment 500A in FIG. 5A employs one transfer lens 533 and one field lens 534 between the source-conversion unit 220 and the objective lens 131 in comparison with FIG. 1B. Accordingly the transfer lens 533, the field lens 534 and the objective lens 131 constitute the primary projection imaging system. FIG. 5B shows the paths of the three beamlets 102_1~102_3. The movable condenser lens 210 collimates the primary electron beam 102 to be normally incident onto the source-conversion unit 220. The beam-limit openings 121_1~121_3 divide the primary electron beam 102 into one on-axis beamlet 102_1, and two off-axis beamlets 102_2 and 102_3. The two off-axis electron optics elements 122_2 and 122_3 deflect the beamlets 102_2 and 102_3 respectively towards the optical axis 500_1. Consequently three first virtual images of the single electron source 101 are formed. Then the transfer lens 533 focuses the three beamlets 102_1~102_3 onto the intermediate image plane PP1, i.e. projecting the three first virtual images thereon. Accordingly three second real images 102_1m, 102_2m and 102_3m of the single electron source 101 are formed. The field lens 534 is located at the intermediate image plane PP1, and bends the off-axis beamlets 102_2 and 102_3 toward the optical axis 500_1 without influencing the focus situations thereof. After that, the objective lens 131 focuses the three beamlets 102_1~102_3 onto the sample surface 7, i.e. projecting the three second real images 102_1m~102_3m thereon. Consequently, on the sample surface 7, the three beamlets 102_1~102_3 form three probe spots 102_1s, 102_2s and 102_3s respectively.

Figure 5C:
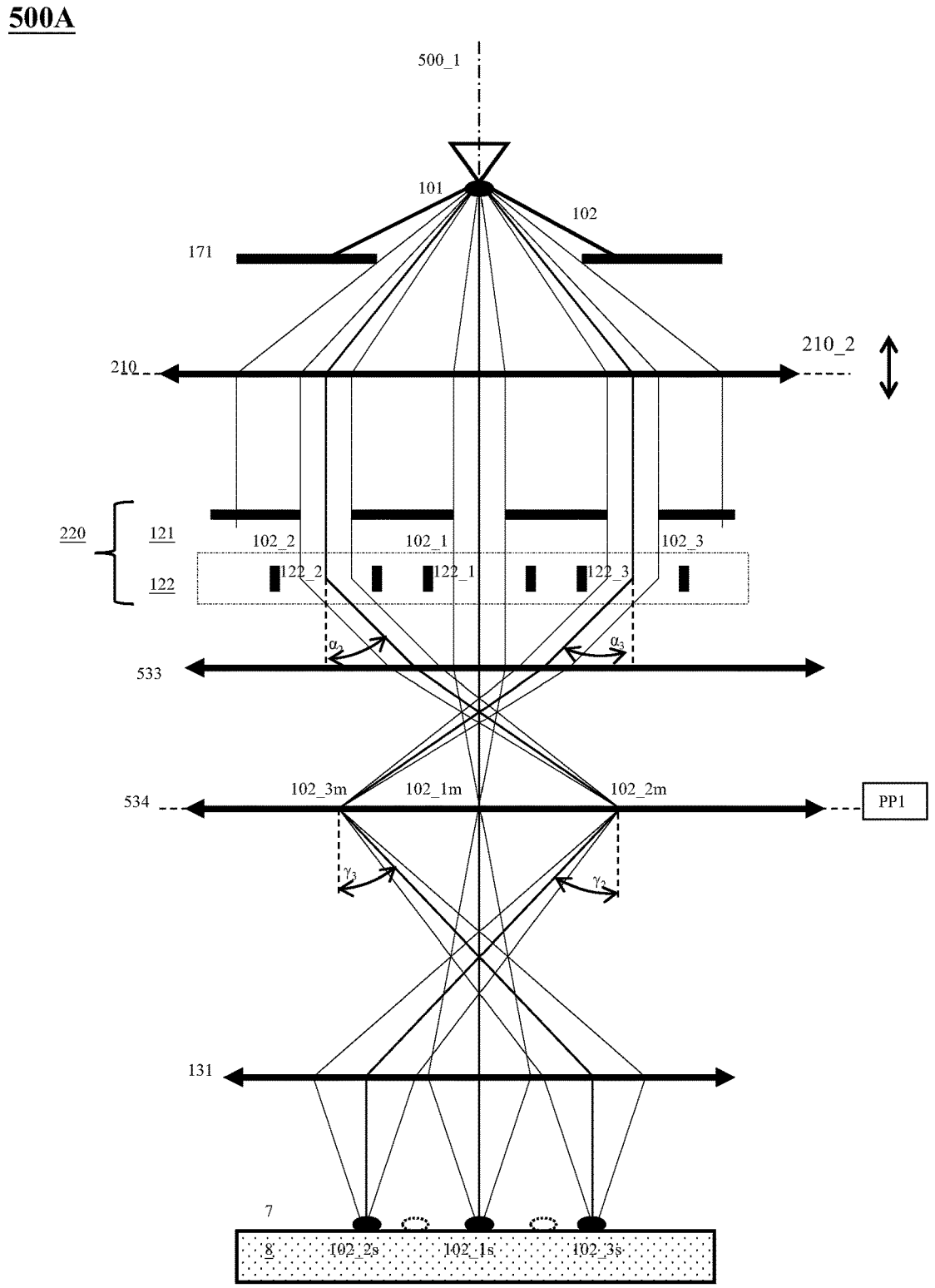

In FIG. 5B, the bending angles $\gamma_2$ and $\gamma_3$ of the beamlets 102_2 and 102_3 due to the field lens 534 are set to minimize the off-axis aberrations of the probe spots 102_2s and 102_3s, and the beamlets 102_2 and 102_3 accordingly pass through or approach the front focal point of the objective lens 131, i.e. forming a crossover CV on the optical axis 500_1 and on or close to the front focal plane thereof. The pitch Ps between the probe spots 102_1s and 102_2s is determined by the bending angle $\gamma_2$ and the first focal length f of the objective lens 131, and can be simply expressed as $Ps \approx \gamma_2 \cdot f$. Similarly, the pitch Ps between the probe spots 102_1s and 102_3s can be simply expressed as $Ps \approx \gamma_3 \cdot f$. The bending angles $\gamma_2$ and $\gamma_3$ change with the radial shifts of the second real images 102_2m and 102_3m, and the radial shifts change with the deflection angles $\alpha_2$ and $\alpha_3$ of beamlets 102_2 and 102_3 due to the electron optics elements 122_2 and 122_3. Therefore the two pitches can be varied by adjusting the deflection angles $\alpha_2$ and $\alpha_3$. In FIG. 5C, the deflection angles $\alpha_2$ and $\alpha_3$ are larger than in FIG. 5B. Consequently the two off-axis probe spots 102_2S and 102_3S are moved away from the previous positions (shown in dash line) in FIG. 5B to the current positions, and the pitches become larger.

In the embodiment 600A in FIG. 6A, the first principal plane 631_2 of the objective lens 631 can be shifted along the optical axis 600_1 within the variation range 631_2r. The axial shift can be done by mechanically moving the position of the objective lens 631 or electrically changing the shape and/or position of the objective lens field. As the first principal plane is closer to the sample surface 7, the first focal length f will become small and the first focal plane will move toward the surface 7. In addition, as the first focal plane moves down, the deflection angles of the plural beamlets decrease. Accordingly the pitches of the plural probe spots will decrease.

Figure 6B:
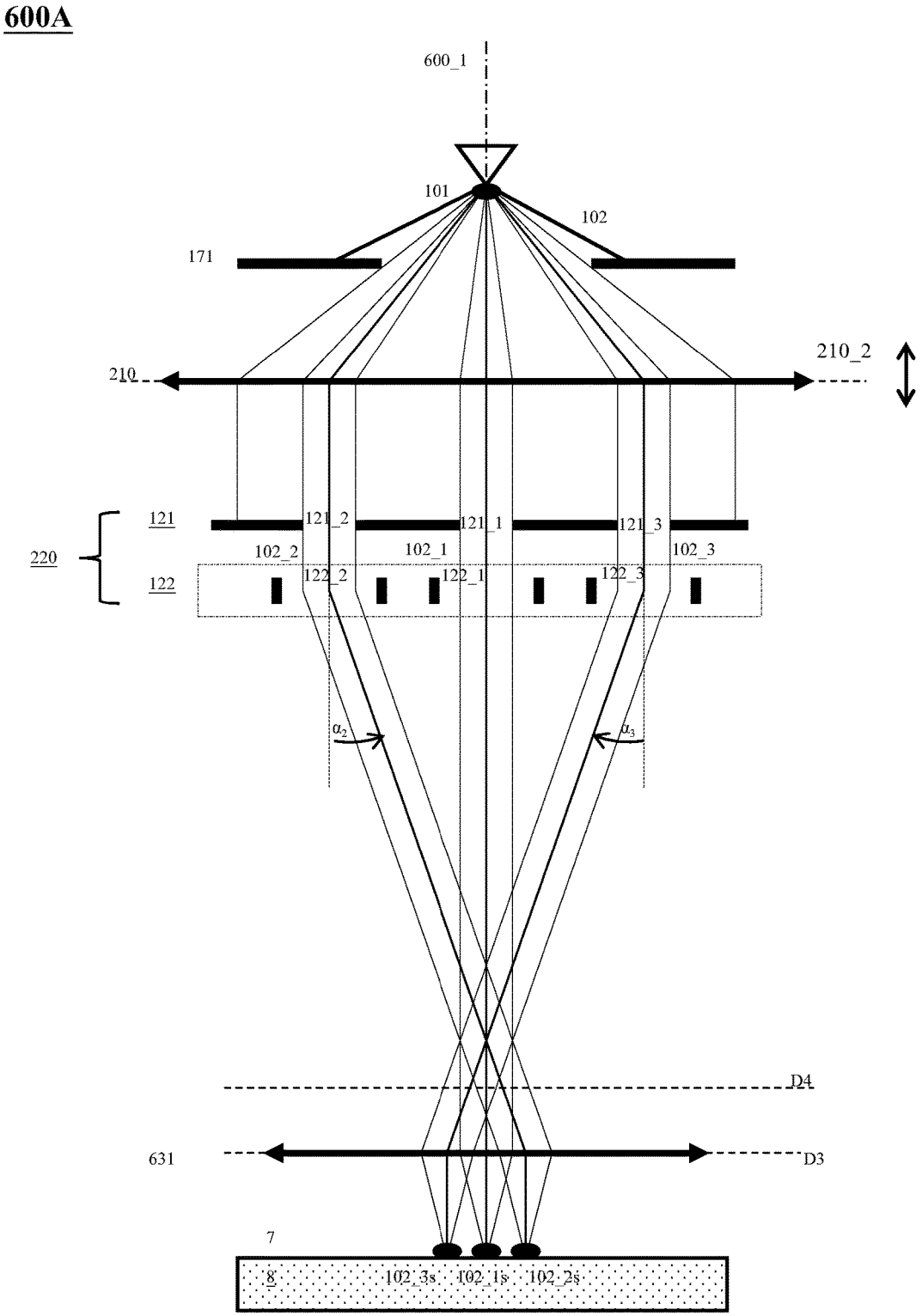
FIGS. 6B and 6C are schematic illustrations of varying the size of the total FOV in accordance with the embodiment in FIG. 6A.
Figure 6C:
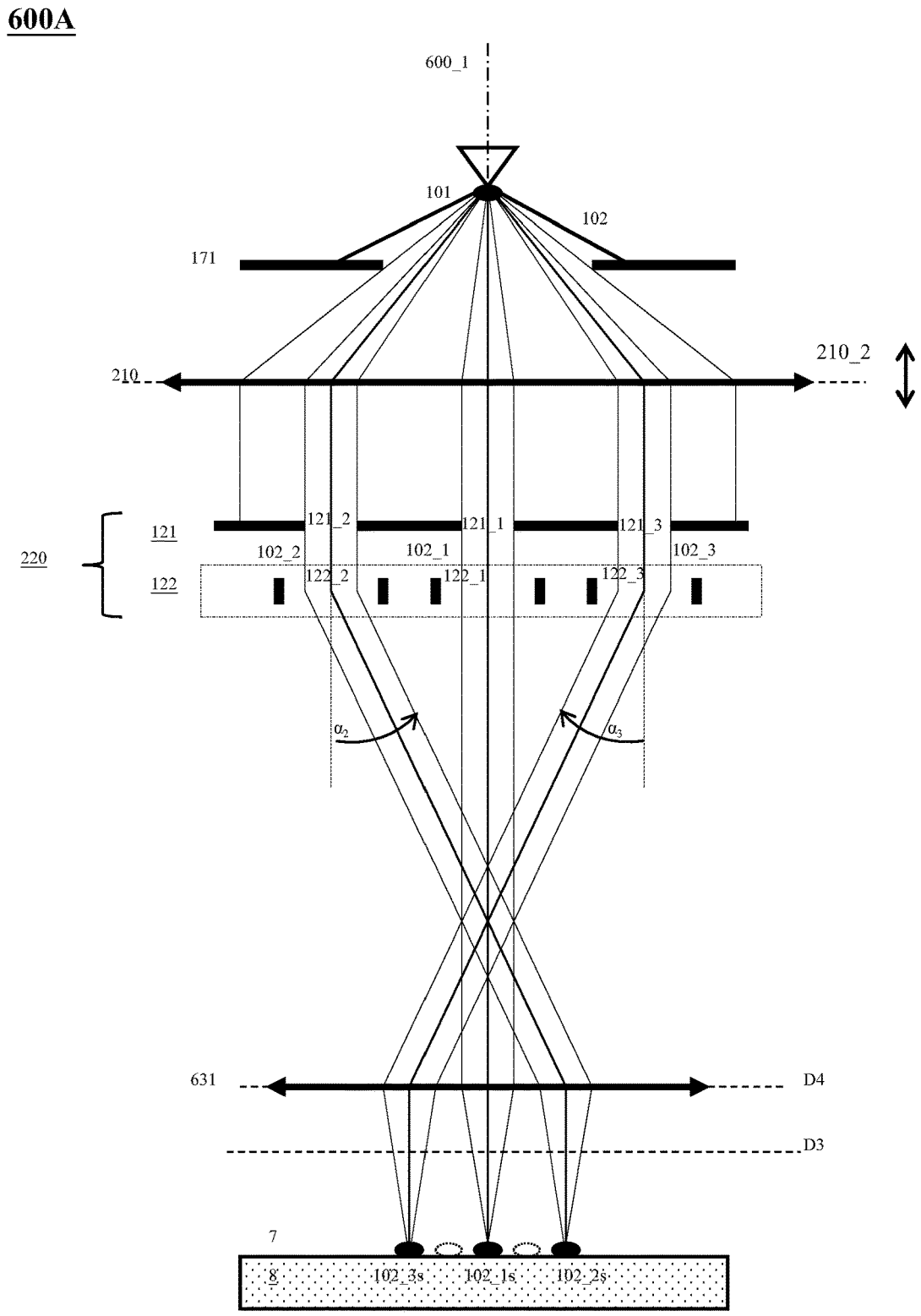

FIGS. 6B and 6C show the paths of the three beamlets when the first principal plane 631_2 is respectively on the position D3 and the position D4. The position D3 is closer to the sample surface 7 than the position D4. Accordingly, the first focal length f and the deflection angles $\alpha_2$ and $\alpha_3$ of the beamlets 102_2 and 102_3 in FIG. 6B are smaller than in FIG. 6C. In FIG. 6C, the probe spots 102_2s and 102_3s move outside from the previous positions (dash line) in FIG. 6B, and the two pitches become larger than in FIG. 6B.

The objective lens in one conventional multi-beam apparatus is an electromagnetic compound lens, as one embodiment 131-1 shown in FIG. 1C. The objective lens comprises one magnetic lens and one electrostatic lens, and works in a retarding mode (the landing energy of an electron is lower than the energy of the electron passing through the objective lens) due to low geometric aberrations and low radiation damage on the sample. The magnetic lens is configured by the coil 131_c1 and the yoke 131_y1 with the pole-pieces 131_mp1 and 131_mp2, and the electrostatic lens is formed by the pole-piece 131_mp1, the field-control electrode 131_e1 and the sample 8. The potential of the inner pole-piece 131_mp1 is higher than the sample 8. The potential of the field-control electrode 131_e1 is set to control the electric field on the sample surface. The electric field can ensure the sample free of electrical breakdown, reduce the geometric aberrations of the plural probe spots, control the charge-up on the sample surface 7 by reflecting back a part of secondary electrons or enhance the collection of secondary electron beams. In FIG. 1C, the shape of the magnetic field is not variable, and the shape of the electrostatic field can only be changed within a limited range. Hence the conventional objective lens is almost not electrically (changing the potentials of the electrodes and/or the excitation current of the coil) movable.

Figure 7A:
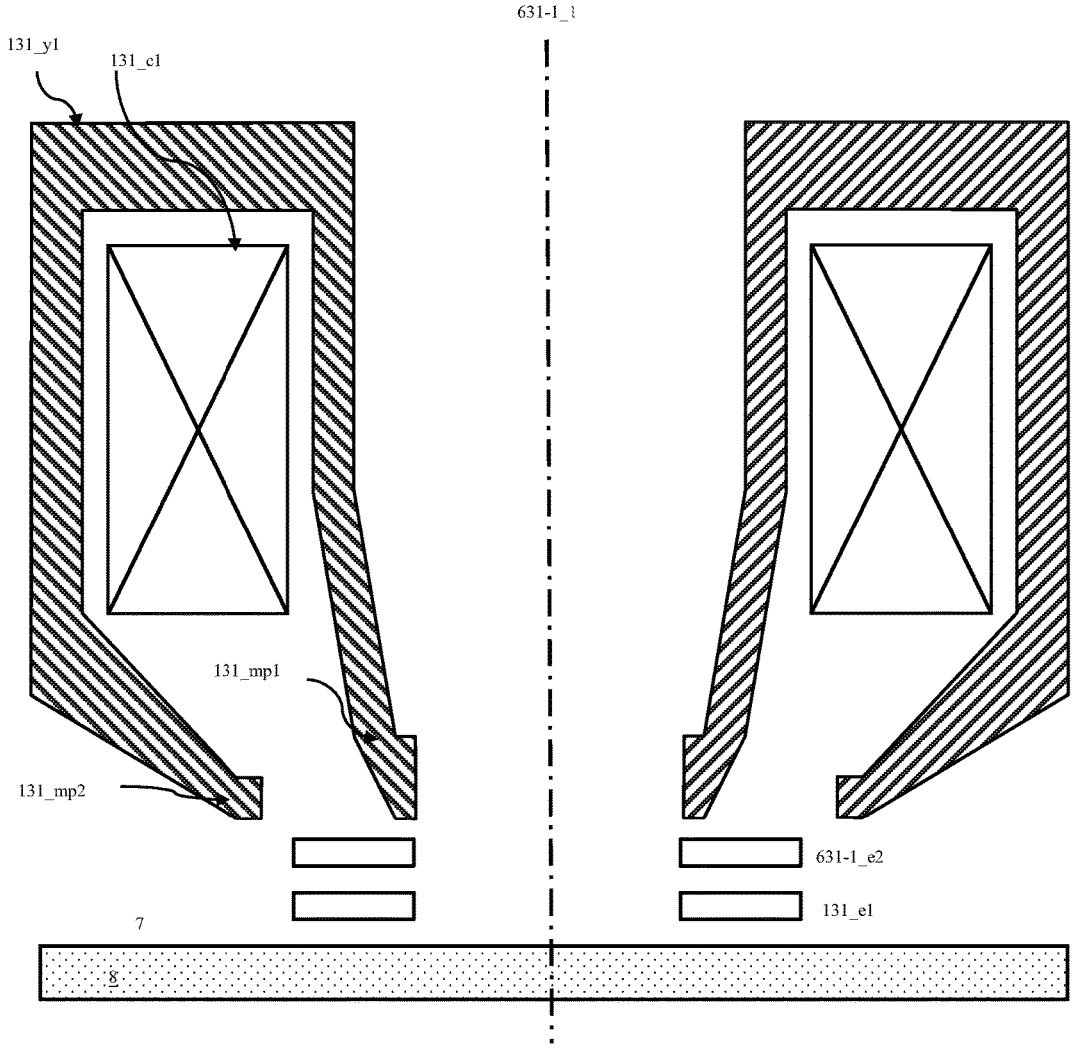
FIGS. 7A-7C are illustrations of three configurations of the movable objective lens in FIG. 6A in accordance with another three embodiments of the present invention.
Figure 7B:
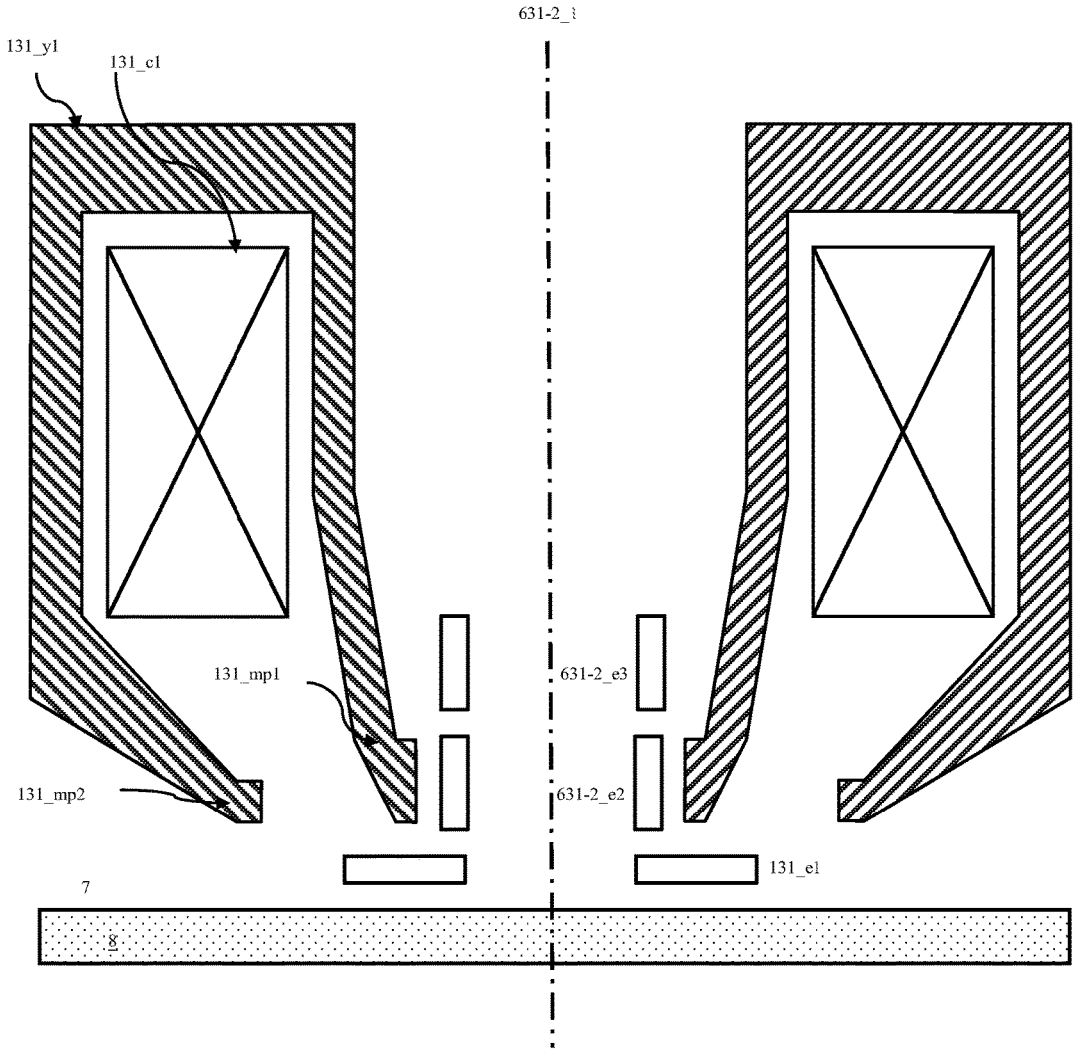
Figure 7C:
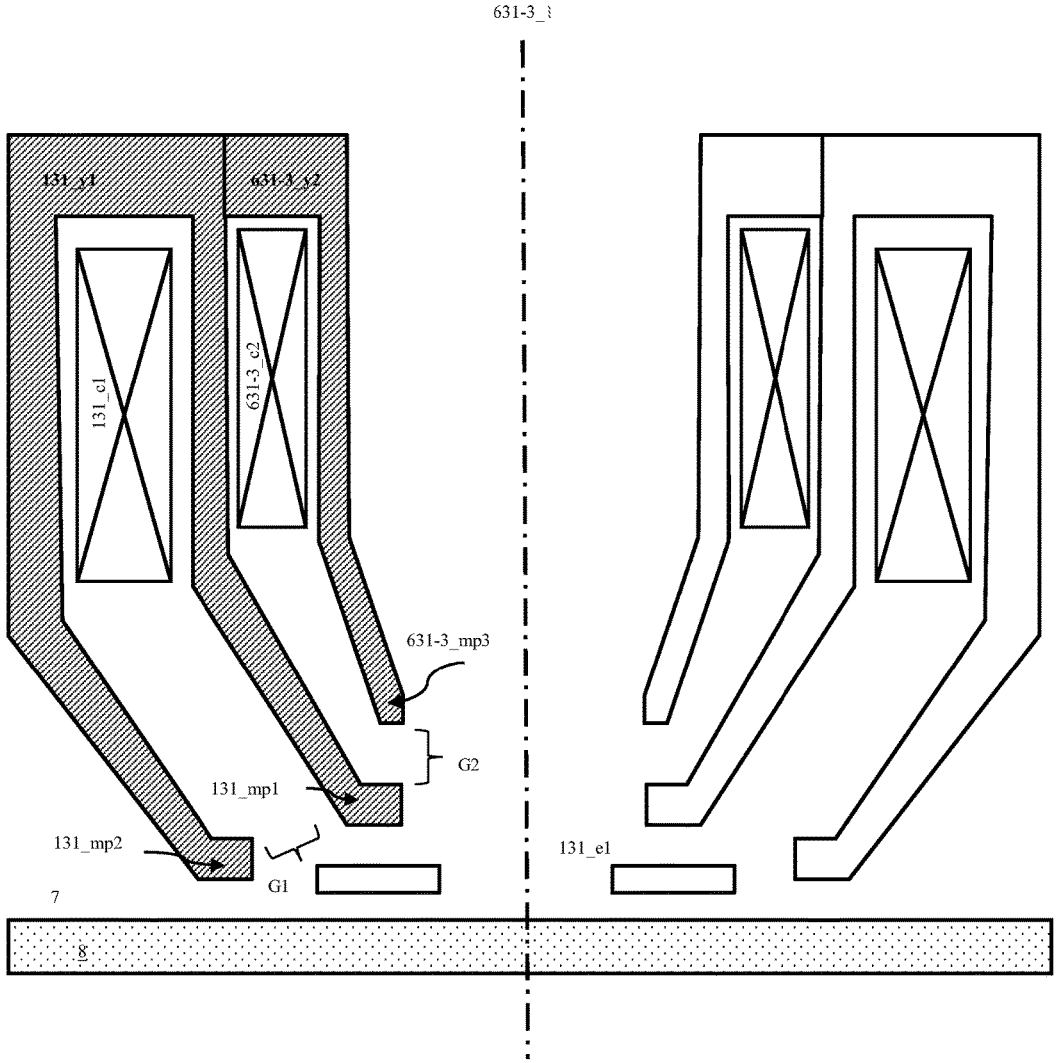

Next three solutions for configuring the movable objective lens 631 are proposed in terms of the conventional objective lens 131-1 in FIG. 1C, and respectively shown in FIGS. 7A, 7B and 7C. In FIG. 7A, the embodiment 631-1 comprises one more electrode 631-1_e2 between the inner pole-piece 131_mp1 and the field-control electrode 131_e1 in comparison with FIG. 1C. Accordingly the electrostatic lens is formed by the inner pole-piece 131_mp1, the electrode 631-1_e2, the field-control electrode 131_e1 and the sample 8. The electrostatic field shape of the electrostatic lens can be varied by adjusting the potential of the electrode 131_e1 and the potential of the electrode 631-1_e2 as well. As the potential of the electrode 631-1_e2 is adjusted to approach the potential of the inner pole-piece 131_mp1, the electrostatic field is squeezed towards the sample, which is equal to moving the objective lens 631-1 towards the sample 8. Accordingly the electrode 631-1_e2 can be called as a field-moving electrode.

In FIG. 7B, the embodiment 631-2 comprises two more electrodes 631-2_e2 and 631-2_e3 inside the bore of the yoke 131_y1 and above the field-control electrode 131_e1 in comparison with FIG. 1C. Accordingly the electrostatic lens is formed by the electrodes 631-2_e3 and 631-2_e2, the field-control electrode 131_e1 and the sample 8. The potential of the electrodes 631-2_e3 is higher than the sample and can be equal to the inner pole-piece 131_mp1. The electrostatic field shape of the electrostatic lens can be varied by adjusting the potential of the electrode 131_e1 and the potential of the electrode 631-2_e2 as well. Similar to FIG. 7A, as the potential of the electrode 631-2_e2 is adjusted to approach the potential of the electrodes 631-1_e3, the electrostatic field is squeezed towards the sample 8, which is equal to moving the objective lens 631-2 towards the sample 8. Accordingly the electrode 631-2_e2 can be called as a field-moving electrode. In comparison the embodiment 631-1 with FIG. 7A, the magnetic lens can be placed closer to the sample 8, and thereby providing a deeper magnetic immersion to the sample so as to generate lower aberrations.

In FIG. 7C, the embodiment 631-3 comprises one more coil 631-3_c2 and one more yoke 631-3y2 inside the bore of the yoke 131_y1 and above the inner pole-piece 131_mp1 in comparison with FIG. 1C. Accordingly one lower magnetic lens, one upper magnetic lens and one electrostatic lens are formed. The lower magnetic lens generates one lower magnetic field by the coil 131_c1 through the lower magnetic-circuit gap G1 between the inner and outer pole-pieces 131_mp1 and 131_mp2 of the yoke 131_y1, while the upper magnetic lens forms one upper magnetic field by the coil 631-3_c2 through the magnetic-circuit gap G2 between the inner pole-piece 131_mp1 and the upper pole-piece 631-3_mp3 of the yoke 631-3_y2. The electrostatic lens is formed by the inner pole-piece 131_mp1, the field-control electrode 131_e1 and the sample 8. The distribution shape of the total magnetic field of the objective lens 631-3 changes with the combination of the upper and lower magnetic fields, therefore can be varied by adjusting the excitation ratio of the upper and lower magnetic lenses or the current ratio of the coils 131_c1 and 631-3_c2. As the current ratio is adjusted higher, the total magnetic field of the objective lens 631-3 is squeezed towards the sample, which is equal to moving the objective lens 631-3 towards the sample 8. Two extreme examples are the total magnetic field of the objective lens 631-3 locates the superior top when the coil 131_c1 turns off and the coil 631-3-c2 turn on, and the lowest when the coil 131_c1 turns on and the coil 631-3_c2 turns off. Each of the solutions in FIGS. 7A and 7B can be combined with the solution in FIG. 7C to configure more embodiments of the movable objective lens 631.

Next some methods of intentionally rotating the probe spot array will be proposed, which can be used to eliminate the orientation variation of the total FOV with respect to changes in the observing conditions and/or accurately match the orientations of sample patterns and the probe spot array. As mentioned above, the objective lens in one conventional multi-beam apparatus is typically an electromagnetic compound lens, such as the embodiment 131-1 shown in FIG. 1C. Therefore appropriately combining the focusing powers of the magnetic lens and the electrostatic lens can rotate the probe spot array around the optical axis to a certain degree. For example, if the objective lens 131 in FIG. 1A is similar to the embodiment 131-1 in FIG. 1C, the field-control electrode 131_e1 can be used to control the rotation of the probe spots 102_2 and 102_3s to a certain degree as well as controlling the electrical field on the surface 7. To keep the electrical field on the surface 7 weaker than a permissible value for the specimen safety, the potential of the field-control electrode 131_e1 can be varied within one specific range, such as −3 kV~5 kV with respect to the sample 8. The focusing power of the electrostatic lens changes with the potential of the field-control electrode 131_e1, and accordingly the focusing power of the magnetic lens needs being changed to keep the plural beamlets focused on the sample surface 7. The focusing power variation of the magnetic lens changes the rotation angles of the probe spots 102_2s and 102_3s. Hence, the rotation angles of the probe spots 102_2s and 102_3s can be adjusted by varying the potential of the field-control electrode 131_e1 within the specific range.

For each of the foregoing embodiments 300A, 400A and 500A of the new apparatus in FIGS. 3A, 4A and 5A, if the objective lens 131 has a configuration similar to the embodiment 131-1, the orientation of the probe spot array can be adjusted by this method. For the embodiment 600A of the new apparatus in FIG. 6A, if the movable objective lens 631 has a configuration similar to one of the embodiments 631-1, 631-2 and 631-3 in FIGS. 7A-7C, the field-control electrode 131_e1 and/or the corresponding field-moving electrode can be used to control the rotation of the probe spot array. For the embodiment 631-3, the orientation can also be changed by varying the polarities of the magnetic fields of the upper magnetic lens and the lower magnetic lens. As well known, for a magnetic lens, the rotation angle is related to the polarity of the magnetic field but the focusing power is not. When the polarities of the magnetic fields of the upper magnetic lens and the lower magnetic lens are same, the upper magnetic lens and the lower magnetic lens rotate the probe spot array in a same direction. When the polarities are opposite to each other, the upper magnetic lens and the lower magnetic lens rotate the probe spot array in opposite directions. Hence the embodiment 631-3 can generate two different orientations of the probe spot array with respect to a required focusing power and the corresponding position of the first principal plane.

Figure 8A:
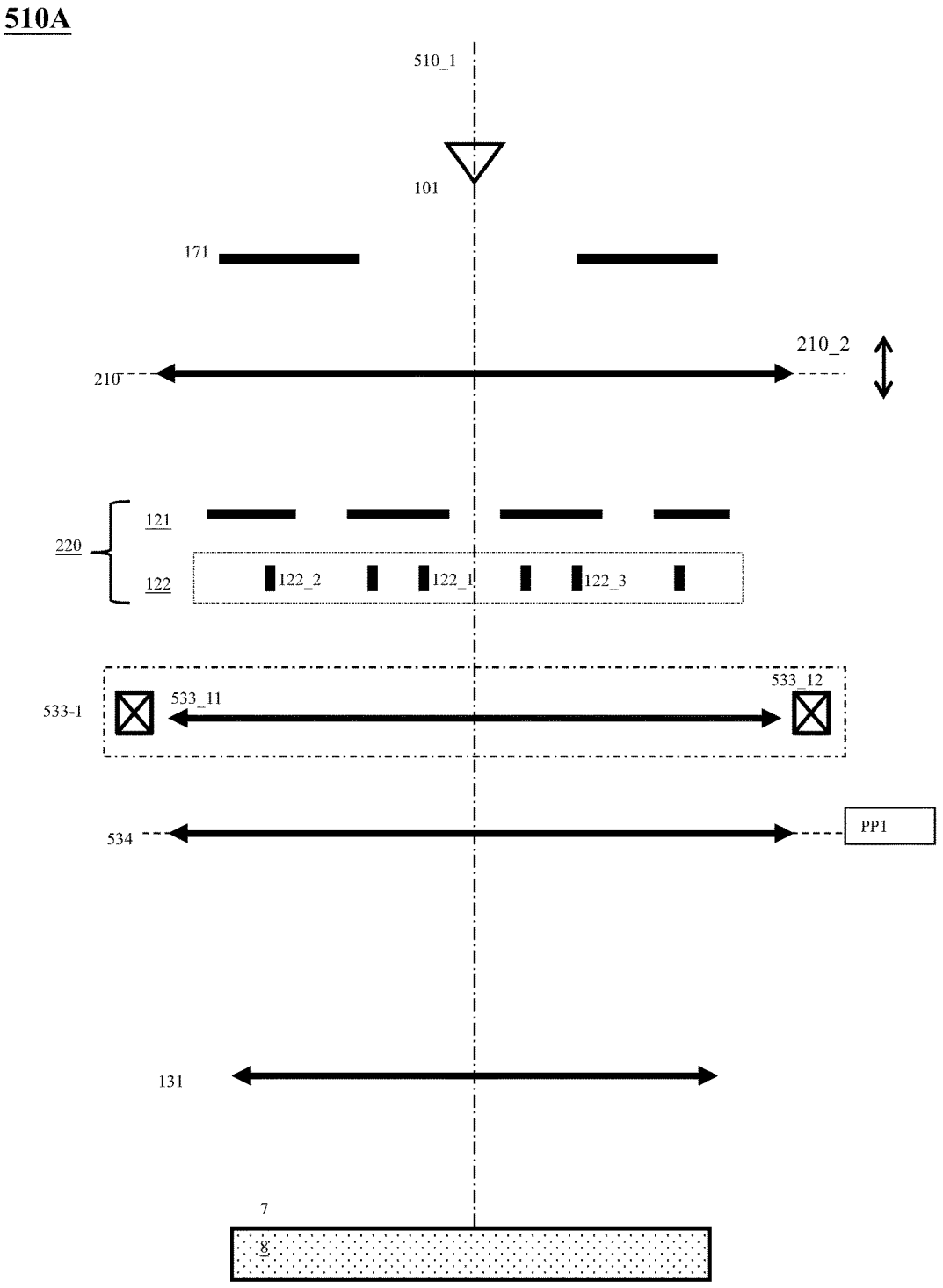
FIGS. 8A and 8B are schematic illustrations of another two configurations of the new multi-beam apparatus in accordance with another two embodiments of the present invention.
Figure 8B:
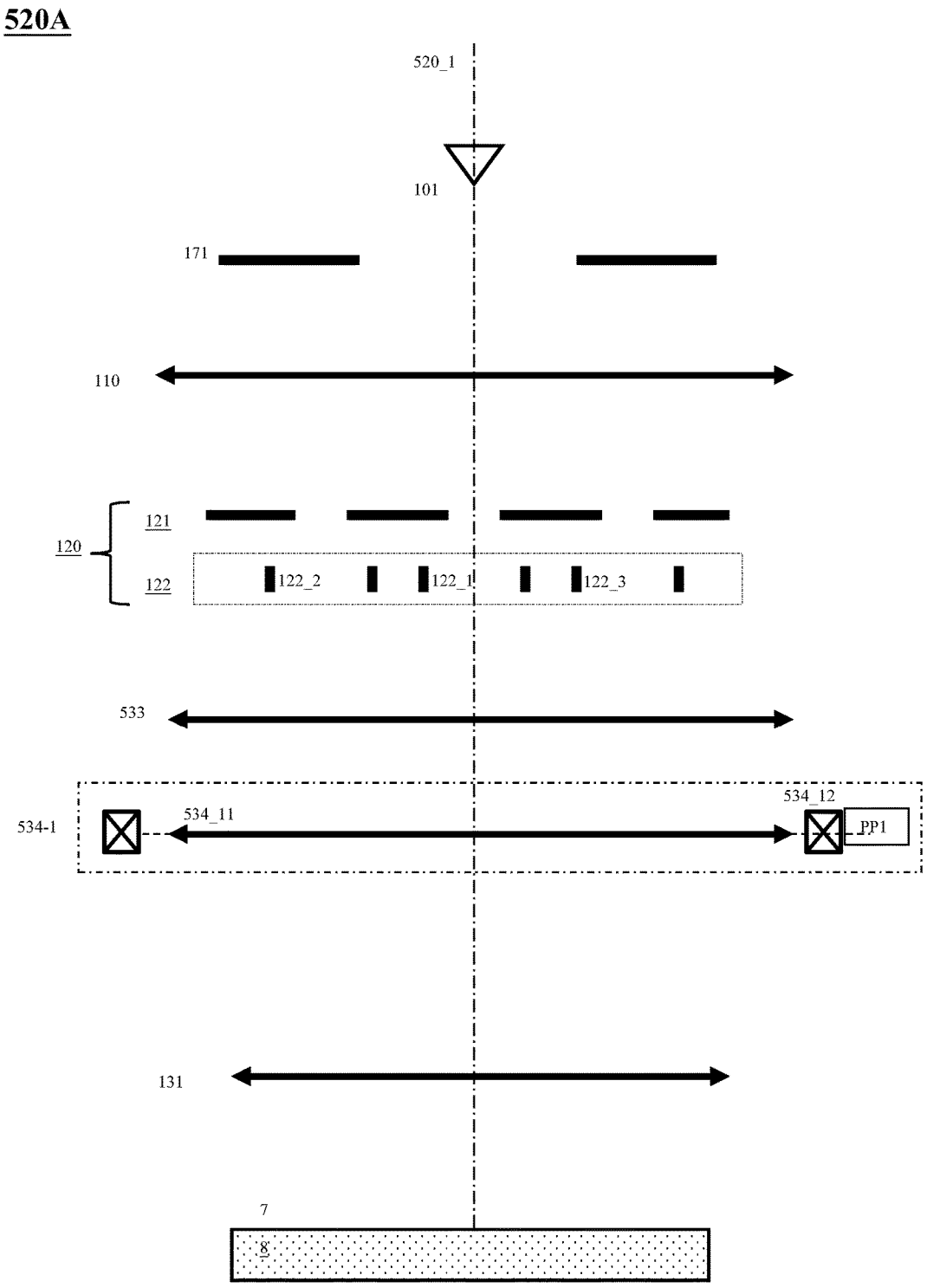

For the embodiment 500A in FIG. 5A, the transfer lens 533 and the field lens 534 provide more possibilities to control the rotation of the probe spot array. One embodiment 510A is shown in FIG. 8A, wherein the electromagnetic compound transfer lens 533-1 comprises one electrostatic transfer lens 533_11 and one magnetic transfer lens 533_12. The magnetic field of the magnetic transfer lens 533_12 can be adjusted to change the rotation of the probe spot array, and the electrostatic field of the electrostatic transfer lens 533_11 can be accordingly varied to keep the three second real images 102_1m, 102_2m and 102_3m on the intermediate image plane PP1. Another embodiment 520A is shown in FIG. 8B, wherein the electromagnetic compound field lens 534-1 comprises one electrostatic field lens 534_11 and one magnetic field lens 534_12. The magnetic field of the magnetic field lens 534_12 can be adjusted to change the rotation of the probe spot array, and the electrostatic field of the electrostatic field lens 534_11 can be accordingly varied to generate the required bending angles of the plural beamlets.

In each of the foregoing embodiments, the plural beamlets are normal or substantially normal incident onto the sample surface, i.e. the incident angles or landing angles (angles formed with the normal of the sample surface) of the plural beamlets are approximately equal to zero. To effectively observe some patterns of a sample, the incident angles are better a little larger than zero. In this case, to ensure plural beamlets perform alike, the plural beamlets are required to have same incident angles. To do so, the crossover CV of the plural beamles needs to be shifted away from the optical axis. The shift of the crossover CV can be done by the image-forming means or one additional beamlet-tilting deflector.

Figure 9A:
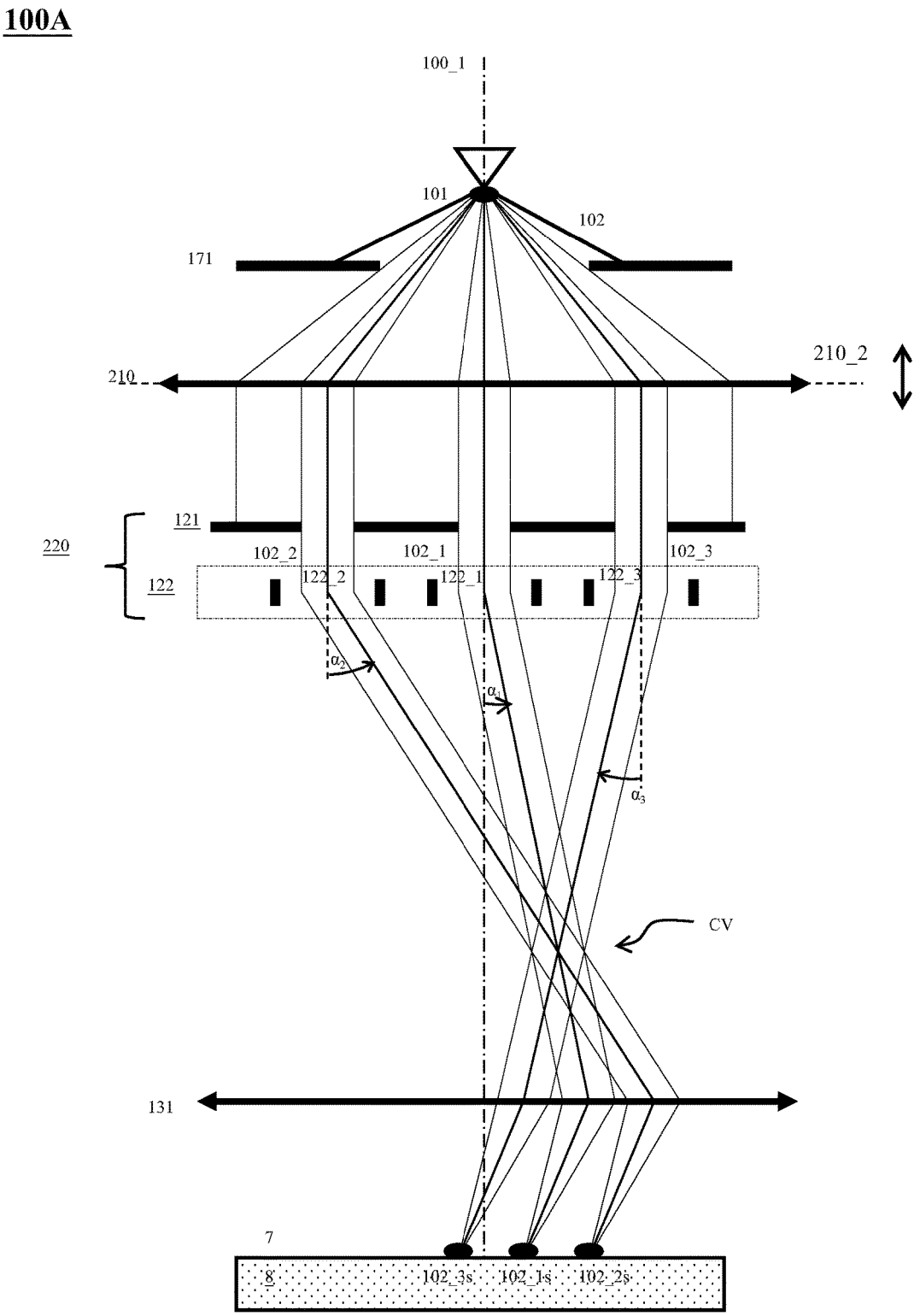
FIG. 9A is a schematic illustration of tilting the plural beamlets in the conventional multi-beam apparatus in FIG. 1B in accordance with another embodiment of the present invention.
Figure 9B:
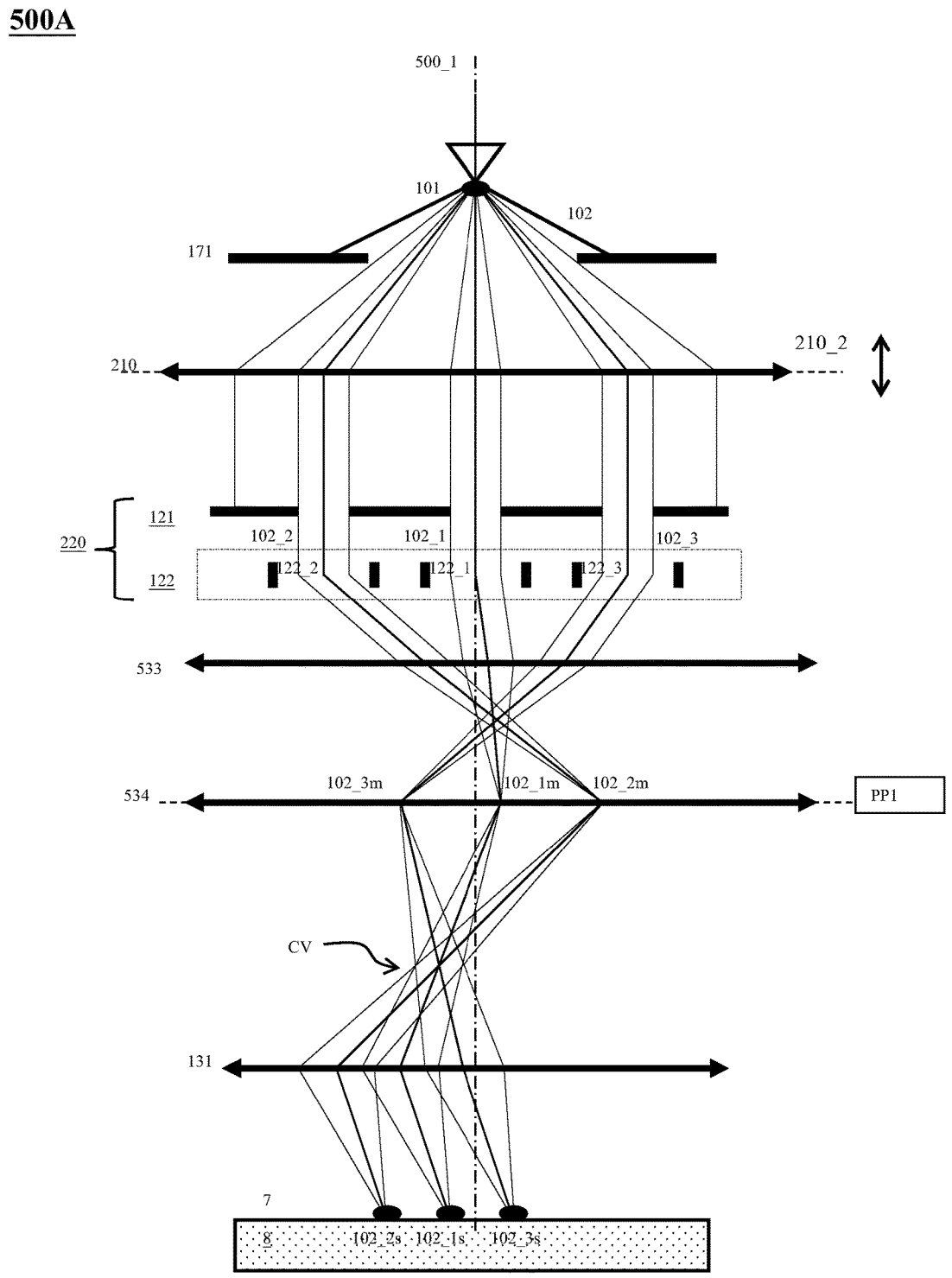
FIG. 9B is a schematic illustration of tilting the plural beamlets in the new multi-beam apparatus in FIG. 5A in accordance with another embodiment of the present invention.

FIG. 9A shows how to tilt the plural beamlets 102_1~102_3 by the image-forming means 122 in the conventional multi-beam apparatus 200A. In comparison with FIG. 1B, the deflection angles $\alpha$1 (equal to zero in FIG. 1B), $\alpha$2 and $\alpha$3 of the beamlets 102_1~102_3 respectively are added same or substantially same amounts so that the crossover CV of the beamlets 102_1~102_3 is shifted away from the optical axis 100_1 and on or close to the first focal plane of the objective lens 131. Accordingly the beamlets 102_1~102_3 obliquely land on the surface 7 with same or nearly same landing angles. The plural beamlets 102_1~102_3 in each of the embodiments 300A, 400A, 500A and 600A can be tilted by the corresponding image-forming means in the same way. For the embodiments 300A, 400A and 600A, the paths of plural beamlets 102_1~102_3 will be similar to those in FIG. 9A. For the embodiment 500A, the paths will be different, as shown in FIG. 9B. In comparison with FIG. 5B, the deflection angles $\alpha$1 (equal to zero in FIG. 5B), $\alpha$2 and $\alpha$3 of the beamlets 102_1~102_3 shift the three second real images 102_1m, 102_2m and 102_3m same or substantially distances on the intermediate image plane PP1. Accordingly the crossover CV of the beamlets 102_1~102_3 after bended by the field 534, is still on or close to the first focal plane but shifted away from the optical axis 500_1.

Figure 10:
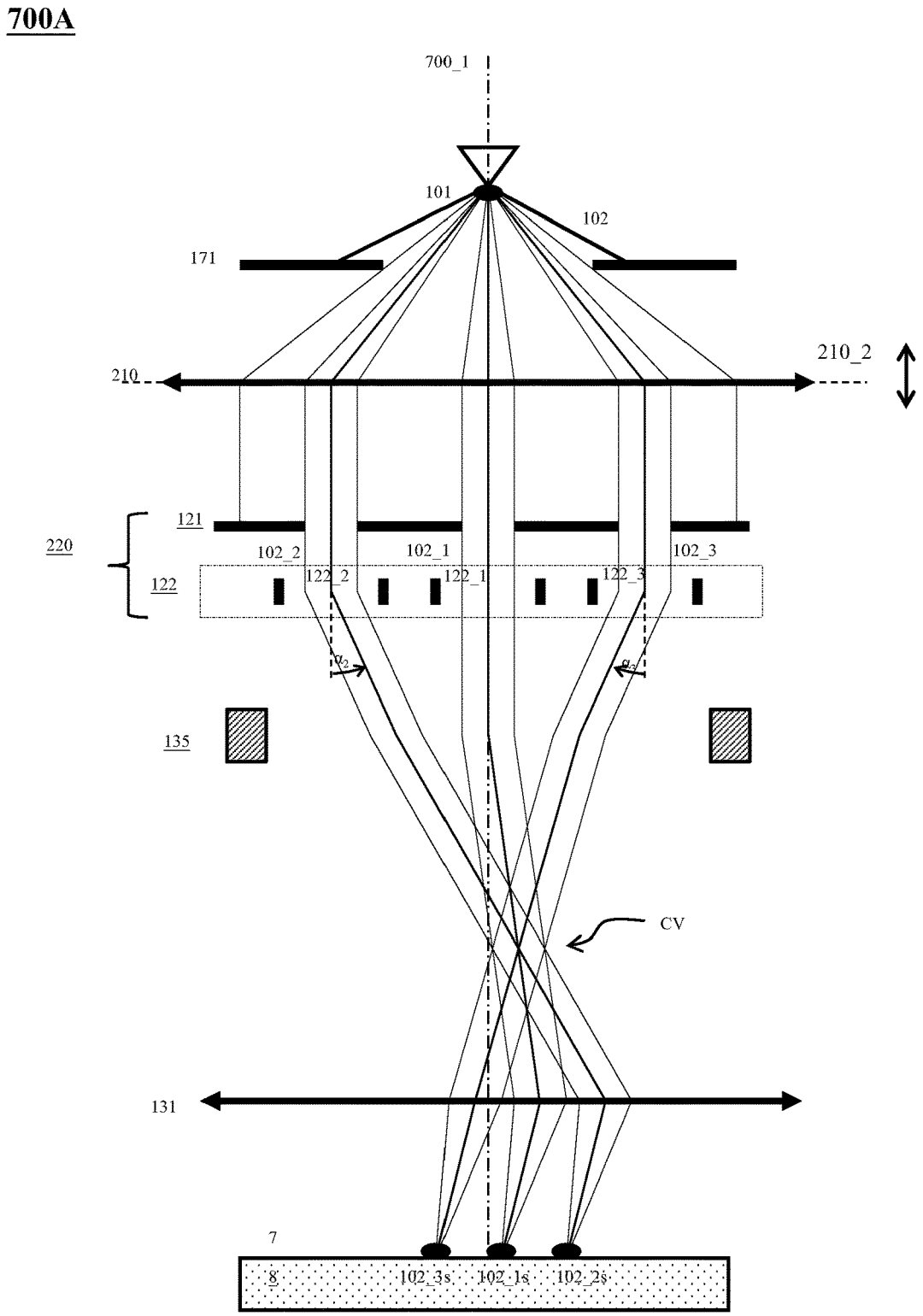
FIG. 10 is a schematic illustration of another configuration of the new multi-beam apparatus in accordance with another embodiment of the present invention.

FIG. 10 shows how to tilt the plural beamlets 102_1~102_3 by one beamlet-tilting deflector 135 in one embodiment 700A of the new apparatus. In comparison with FIG. 1B, the beamlet-tilting deflector 135 deflects the beamlets 102_1~102_3 together to shift the crossover CV away from the optical axis 700_1 and on or close to the front focal plane of the objective lens 131. Similarly, one beamlet-tilting deflector can also be added to the embodiments 300A, 400A, 500A and 600A for tilting the plural beams together. The beamlet-tilting deflector can be placed between the source-conversion unit and the front focal plane of the objective lens, and is preferred close to the source-conversion unit. In addition, if the deflection scanning unit in one of the foregoing embodiments is above the front focal plane of the objective lens, it can shift the crossover of the plural beamlets and the additional beamlet-tilting deflector therefore is not needed.

Although each of the foregoing embodiments of the new apparatus only employs one or two of the methods for varying the total FOV in size, orientation and incident angle, the methods can be combined in many ways. For example the new apparatus can use one movable image-forming means and one movable objective lens together, or use one movable objective lens, one transfer lens and one field lens together. Although the methods are shown and explained by taking the embodiment 200A in FIG. 1B as an example, the methods can be applied to the other embodiments (such as the embodiment 100A in FIG. 1A) of the conventional apparatuses to configure more embodiments of the new multi-beam apparatus.

In summary, based on the conventional multi-beam apparatuses proposed in the CROSS REFERENCE, this invention proposes several methods to configure a new multi-beam apparatus whose total FOV is variable in size, orientation and incident angle. Hence the new apparatus provides more flexibility to speed the sample observation and enable more kinds of samples observable. More specifically, the new apparatus can be used as a yield management to provide more possibilities to achieve a high throughput and detect more kinds of defects. Three methods are proposed to change the pitches of the plural beamlets on the sample surface for varying the size of the total FOV, i.e. using a movable image-forming means in the source-conversion unit, using a movable objective lens, and using a transfer lens and a field lens between the source-conversion unit and the objective lens. Three methods are employed to intentionally rotate the probe spot array for varying the orientation of the total FOV, i.e. using an electromagnetic compound objective lens and varying the electric field thereof, using one objective lens with two magnetic lenses and setting the magnetic fields thereof opposite in polarity, and using one magnetic lens in either or both of the transfer lens and the field lens. Three methods are proposed to shift the crossover of the plural beamlets away from the optical axis for equally varying the landing angles of the plural beamlets on the sample surface. The shift can be done by the image-forming means, or one additional beamlet-tilting deflector, or the deflection scanning unit.

Although the present invention has been explained in relation to its preferred embodiment, it is to be understood that other modifications and variation can be made without departing the spirit and scope of the invention as hereafter claimed.

What is claimed is:

1. A multi-beam apparatus for observing a surface of a sample, comprising:

an electron source;

a condenser lens below said electron source;

a source-conversion unit below said condenser lens;

an objective lens below said source-conversion unit;

a deflection scanning unit below said source-conversion unit;

a sample stage below said objective lens;

a beam separator below said source-conversion unit;

a secondary projection imaging system; and an electron detection device with a plurality of detection elements, wherein said electron source, said condenser lens and said objective lens are aligned with a primary optical axis of said apparatus, and said sample stage sustains said sample so that said surface faces to said objective lens, wherein said source-conversion unit comprises a beamlet-limit means with a plurality of beam-limit openings, and an image-forming means with a plurality of electron optics elements and movable along said primary optical axis, wherein said electron source generates a primary-electron beam along said primary optical axis and said condenser lens focuses said primary-electron beam, wherein a plurality of beamlets of said primary-electron beam pass through said plurality of beam-limit openings respectively, and is deflected by said plurality of electron optics elements towards said primary optical axis to form a plurality of virtual images of said electron source respectively, wherein said plurality of beamlets is focused by said objective lens onto said surface and therefore forms a plurality of probe spots thereon respectively, and said deflection scanning unit deflects said plurality of beamlets to scan said plurality of probe spots respectively over a plurality of scanned regions within an observed area on said surface, wherein a plurality of secondary electron beams is generated by said plurality of probe spots respectively from said plurality of scanned regions and directed into said secondary projection imaging system by said beam separator, said secondary projection imaging system focuses and keeps said plurality of secondary electron beams to be detected by said plurality of detection elements respectively, and each detection element therefore provides an image signal of one corresponding scanned region.

2. The apparatus according to claim 1, wherein deflection angles of said plurality of beamlets due to said plurality of electron optics elements are respectively set to reduce off-axis aberrations of said plurality of probe spots.

3. The apparatus according to claim 2, wherein pitches of said plurality of probe spots are varied together by moving said image-forming means along said primary optical axis.

4. The apparatus according to claim 2, wherein said objective lens comprises a magnetic lens and an electrostatic lens.

5. The apparatus according to claim 4, wherein an orientation of said plurality of probe spots is selectable by varying a ratio of focusing powers of said magnetic lens and said electrostatic lens.

6. The apparatus according to claim 2, wherein said deflection angles ensure said plurality of beamlets to land on said surface perpendicularly or substantially perpendicularly.

7. The apparatus according to claim 2, wherein said deflection angles ensure said plurality of beamlets to obliquely land on said surface with same or substantially same landing angles.

8. The apparatus according to claim 6, wherein said deflection scanning unit is above a front focal plane of said objective lens.

9. The apparatus according to claim 8, wherein said deflection scanning unit tilts said plurality of beamlets to obliquely land on said surface with same or substantially same landing angles.

10. The apparatus according to claim 6, further comprising a beamlet-tilting deflector between said source-conversion unit and a front focal plane of said objective lens.

11. The apparatus according to claim 10, wherein said beamlet-tilting deflector tilts said plurality of beamlets to obliquely land on said surface with same or substantially same landing angles.

[12. A multi-beam apparatus for observing a surface of a sample, comprising:

an electron source;

a condenser lens below said electron source;

a source-conversion unit below said condenser lens;

an objective lens below said source-conversion unit;

a deflection scanning unit below said source-conversion unit;

a sample stage below said objective lens;

a beam separator below said source-conversion unit;

a secondary projection imaging system; and an electron detection device with a plurality of detection elements, wherein said electron source, said condenser lens and said objective lens are aligned with a primary optical axis of said apparatus, and said sample stage sustains said sample so that said surface faces to said objective lens, wherein said source-conversion unit comprises a beamlet-limit means with a plurality of beam-limit openings, a first image-forming means with a plurality of first electron optics elements and a second image-forming means with a plurality of second electron optics elements, said second image-forming means is below said first image-forming means and movable in a radial direction, and one of said first image-forming means and said second image-forming means is used as an active image-forming means, wherein said electron source generates a primary-electron beam along said primary optical axis and said condenser lens focuses said primary-electron beam, wherein a plurality of beamlets of said primary-electron beam pass through said plurality of beam-limit openings respectively, and is deflected by said active image-forming means towards said primary optical axis to form a plurality of virtual images of said electron source respectively, wherein said plurality of beamlets is focused by said objective lens onto said surface and therefore forms a plurality of probe spots thereon respectively, and said deflection scanning unit deflect said plurality of beamlets to scan said plurality of probe spots respectively over a plurality of scanned regions within an observed area on said surface, wherein a plurality of secondary electron beams is generated by said plurality of probe spots respectively from said plurality of scanned regions and directed into said secondary projection imaging system by said beam separator, said secondary projection imaging system focuses and keeps said plurality of secondary electron beams to be detected by said plurality of detection elements respectively, and each detection element therefore provides an image signal of one corresponding scanned region.]

[13. The apparatus according to claim 12, wherein deflection angles of said plurality of beamlets due to said active image-forming means are respectively set to reduce off-axis aberrations of said plurality of probe spots.]

[14. The apparatus according to claim 13, wherein pitches of said plurality of probe spots are varied together by changing said active image-forming means between said first image-forming means and said second image-forming means, and when said first image-forming means is selected, said second image-forming means is moved outside so as not to block said plurality of beamlets.]

[15. The apparatus according to claim 13, wherein said objective lens comprises a magnetic lens and an electrostatic lens.]

[16. The apparatus according to claim 15, wherein an orientation of said plurality of probe spots is selectable by varying a ratio of focusing powers of said magnetic lens and said electrostatic lens.]

[17. The apparatus according to claim 13, wherein said deflection angles ensure said plurality of beamlets to land on said surface perpendicularly or substantially perpendicularly.]

[18. The apparatus according to claim 13, wherein said deflection angles ensure said plurality of beamlets to obliquely land on said surface with same or substantially same landing angles.]

[19. The apparatus according to claim 17, wherein said deflection scanning unit is above a front focal plane of said objective lens.]

[20. The apparatus according to claim 19, wherein said deflection scanning unit tilts said plurality of beamlets to obliquely land on said surface with same or substantially same landing angles.]

[21. The apparatus according to claim 17, further comprising a beamlet-tilting deflector between said source-conversion unit and a front focal plane of said objective lens.]

[22. The apparatus according to claim 21, wherein said beamlet-tilting deflector tilts said plurality of beamlets to obliquely land on said surface with same or substantially same landing angles.]

[23. An multi-beam apparatus for observing a surface of a sample, comprising:

an electron source;

a condenser lens below said electron source;

a source-conversion unit below said condenser lens;

an objective lens below said source-conversion unit;

a deflection scanning unit below said source-conversion unit;

a sample stage below said objective lens;

a beam separator below said source-conversion unit;

a secondary projection imaging system; and an electron detection device with a plurality of detection elements, wherein said electron source, said condenser lens and said objective lens are aligned with a primary optical axis of said apparatus, a first principal plane of said objective lens is movable along said primary optical axis, and said sample stage sustains said sample so that said surface faces to said objective lens, wherein said source-conversion unit comprises a beamlet-limit means with a plurality of beam-limit openings, and an image-forming means with a plurality of electron optics elements, wherein said electron source generates a primary-electron beam along said primary optical axis and said condenser lens focuses said primary-electron beam, wherein a plurality of beamlets of said primary-electron beam pass through said plurality of beam-limit openings respectively, and is deflected by said plurality of electron optics elements towards said primary optical axis to form a plurality of virtual images of said electron source respectively, wherein said plurality of beamlets is focused by said objective lens onto said surface and therefore forms a plurality of probe spots thereon respectively, and said deflection scanning unit deflects said plurality of beamlets to scan said plurality of probe spots respectively over a plurality of scanned regions within an observed area on said surface, wherein a plurality of secondary electron beams is generated by said plurality of probe spots respectively from said plurality of scanned regions and directed into said secondary projection imaging system by said beam separator, said secondary projection imaging system focuses and keeps said plurality of secondary electron beams to be detected by said plurality of detection elements respectively, and each detection element therefore provides an image signal of one corresponding scanned region.]

[24. The apparatus according to claim 23, wherein deflection angles of said plurality of beamlets due to said plurality of electron optics elements are respectively set to reduce off-axis aberrations of said plurality of probe spots.]

[25. The apparatus according to claim 24, wherein pitches of said plurality of probe spots are varied together by moving said first principal plane along said primary optical axis.]

[26. The apparatus according to claim 24, wherein said deflection angles ensure said plurality of beamlets to land on said surface perpendicularly or substantially perpendicularly.]

[27. The apparatus according to claim 24, wherein said deflection angles ensure said plurality of beamlets to obliquely land on said surface with same or substantially same landing angles.]

[28. The apparatus according to claim 26, wherein said deflection scanning unit is above a front focal plane of said objective lens.]

[29. The apparatus according to claim 28, wherein said deflection scanning unit tilts said plurality of beamlets to obliquely land on said surface with same or substantially same landing angles.]

[30. The apparatus according to claim 26, further comprising a beamlet-tilting deflector between said source-conversion unit and a front focal plane of said objective lens.]

[31. The apparatus according to claim 30, wherein said beamlet-tilting deflector tilts said plurality of beamlets to obliquely land on said surface with same or substantially same landing angles.]

[32. The apparatus according to claim 24, wherein said objective lens comprises a lower magnetic lens and an electrostatic lens.]

[33. The apparatus according to claim 32, wherein said electrostatic lens comprises a field-control electrode and a field-moving electrode, and generates an electrostatic field.]

[34. The apparatus according to claim 33, wherein a potential of said field-control electrode is set to control said electrostatic field on said surface for said sample free of electrical breakdown.]

[35. The apparatus according to claim 34, wherein a potential of said field-moving electrode is set to move said electrostatic field for moving said first principal plane.]

[36. The apparatus according to claim 34, wherein an orientation of said plurality of probe spots is selectable by varying either or both of potentials of said field-control electrode and said field-moving electrode.]

[37. The apparatus according to claim 32, further comprising an upper magnetic lens above said lower magnetic lens.]

[38. The apparatus according to claim 37, wherein said first principal plane is moved by varying a ratio of focusing powers of said lower magnetic lens and said upper magnetic lens.]

[39. The apparatus according to claim 37, wherein an orientation of said plurality of probe spots is selectable by setting polarities of magnetic fields of said upper and lower magnetic lenses same or opposite.]

[40. A multi-beam apparatus for observing a surface of a sample, comprising:

an electron source;

a condenser lens below said electron source;

a source-conversion unit below said condenser lens;

a transfer lens below said source-conversion unit;

a field lens below said transfer lens;

an objective lens below said field lens;

a deflection scanning unit below said source-conversion unit;

a sample stage below said objective lens;

a beam separator below said source-conversion unit;

a secondary projection imaging system; and an electron detection device with a plurality of detection elements, wherein said electron source, said condenser lens, said transfer lens, said field lens and said objective lens are aligned with a primary optical axis of said apparatus, and said sample stage sustains said sample so that said surface faces to said objective lens, wherein said source-conversion unit comprises a beamlet-limit means with a plurality of beam-limit openings, and an image-forming means with a plurality of electron optics elements, wherein said electron source generates a primary-electron beam along said primary optical axis and said condenser lens focuses said primary-electron beam, wherein a plurality of beamlets of said primary-electron beam pass through said plurality of beam-limit openings respectively, and is deflected by said plurality of electron optics elements towards said primary optical axis to form a plurality of first virtual images of said electron source respectively, wherein said transfer lens images said plurality of first virtual images onto an intermediate image plane and therefore forms a plurality of second real images respectively thereon, said field lens is placed on said intermediate image plane and bends said plurality of beamlets, said objective lens images said plurality of second real images onto said surface and therefore forms a plurality of probe spots thereon respectively, and said deflection scanning unit deflects said plurality of beamlets to scan said plurality of probe spots respectively over a plurality of scanned regions within an observed area on said surface, wherein a plurality of secondary electron beams is generated by said plurality of probe spots respectively from said plurality of scanned regions and directed into said secondary projection imaging system by said beam separator, said secondary projection imaging system focuses and keeps said plurality of secondary electron beams to be detected by said plurality of detection elements respectively, and each detection element therefore provides an image signal of one corresponding scanned region.]

[41. The apparatus according to claim 40, wherein bending angles of said plurality of beamlets due to said field lens are set to reduce off-axis aberrations of said plurality of probe spots.]

[42. The apparatus according to claim 41, wherein deflection angles of said plurality of beamlets due to said plurality of electron optics elements are adjusted to change pitches of said plurality of probe spots respectively.]

[43. The apparatus according to claim 41, wherein said objective lens comprises a first magnetic lens and a first electrostatic lens.]

[44. The apparatus according to claim 43, wherein an orientation of said plurality of probe spots is selectable by varying a ratio of focusing powers of said first magnetic lens and said first electrostatic lens.]

[45. The apparatus according to claim 41, wherein said transfer lens comprises a second magnetic lens and a second electrostatic lens.]

[46. The apparatus according to claim 45, wherein an orientation of said plurality of probe spots is selectable by varying a ratio of focusing powers of said second magnetic lens and said second electrostatic lens.]

[47. The apparatus according to claim 41, wherein said field lens comprises a third magnetic lens and a third electrostatic lens.]

[48. The apparatus according to claim 47, wherein an orientation of said plurality of probe spots is selectable by varying a ratio of focusing powers of said third magnetic lens and said third electrostatic lens.]

[49. The apparatus according to claim 41, wherein said bending angles and deflection angles of said plurality of beamlets due to said plurality of electron optics elements ensure said plurality of beamlets to land on said surface perpendicularly or substantially perpendicularly.]

[50. The apparatus according to claim 41, wherein said bending angles and deflection angles of said plurality of beamlets due to said plurality of electron optics elements ensure said plurality of beamlets to obliquely land on said surface with same or substantially same landing angles.]

[51. The apparatus according to claim 49, wherein said deflection scanning unit is above a front focal plane of said objective lens.]

[52. The apparatus according to claim 51, wherein said deflection scanning unit tilts said plurality of beamlets to obliquely land on said surface with same or substantially same landing angles.]

[53. The apparatus according to claim 49, further comprising a beamlet-tilting deflector between said source-conversion unit and a front focal plane of said objective lens.]

[54. The apparatus according to claim 53, wherein said beamlet-tilting deflector tilts said plurality of beamlets to obliquely land on said surface with same or substantially same landing angles.]

55. A method to configure a multi-beam apparatus for observing a surface of a sample, comprising steps of:

configuring an image-forming means of a source-conversion unit movable along a primary optical axis thereof, *the image-forming means having a plurality of electron optics elements*;

using said image-forming means to form a plurality of virtual images of an electron source respectively;

using an objective lens to image said plurality of virtual images onto said surface and form a plurality of probe spots thereon; and moving said image-forming means to vary pitches of said plurality of probe spots.

[56. A method to configure a multi-beam apparatus for observing a surface of a sample, comprising steps of:

configuring a source-conversion unit with a first image-forming means and a second image-forming means, wherein said second image-forming means is farther away from an electron source than said first image-forming means and movable in a radial direction of said apparatus;

using one of said first image-forming means and said second image-forming means as an active image-forming means, wherein when said first image-forming means is used, said second image-forming means is moved away;

using said active image-forming means to form a plurality of virtual images of said electron source respectively;

using an objective lens to image said plurality of virtual images onto said surface and form a plurality of probe spots thereon; and changing said active image-forming means between said first image-forming means and said second image-forming means to vary pitches of said plurality of probe spots.]

[57. A method to configure a multi-beam apparatus for observing a surface of a sample, comprising steps of:

configuring an objective lens with a first principal plane movable along a primary optical axis of said apparatus;

using an image-forming means of a source-conversion unit to form a plurality of virtual images of an electron source respectively;

using said objective lens to image said plurality of virtual images onto said surface and form a plurality of probe spots thereon; and moving said first principal plane to vary pitches of said plurality of probe spots.]

[58. A method to configure a multi-beam apparatus for observing a surface of a sample, comprising steps of:

configuring an objective lens with a lower magnetic lens and an electrostatic lens in said apparatus;

using an image-forming means of a source-conversion unit to form a plurality of virtual images of an electron source respectively;

using said objective lens to image said plurality of virtual images onto said surface and form a plurality of probe spots thereon; and changing a ratio of focusing powers of said magnetic lens and said electrostatic lens to select an orientation of said plurality of probe spots.]

[59. The method according to claim 58, further comprising a step of configuring said objective lens with an upper magnetic lens farther away from said surface than said lower magnetic lens.]

[60. The method according to claim 59, further comprising a step of changing polarities of magnetic fields of said upper and lower magnetic lenses to select said orientation.]

[61. A method to configure a multi-beam apparatus for observing a surface of a sample, comprising steps of:

using an image-forming means of a source-conversion unit to deflect a plurality of beamlets from an electron source to form a plurality of first virtual images thereof respectively;

using an objective lens to image said plurality of virtual images onto said surface and form a plurality of probe spots thereon; and setting deflection angles of said plurality of beamlets due to said image-forming means so that said plurality of beamlets lands on said surface with same or substantially same landing angles.]

[62. The method according to claim 61, further comprising a step of changing said deflection angles to equally vary said landing angles.]

[63. The method according to claim 61, further comprising a step of using a deflection scanning unit to tilt said plurality of beamlets so as to equally vary said landing angles.]

[64. The method according to claim 61, further comprising a step of using a beamlet-tilting deflector to tilt said plurality of beamlets so as to equally vary said landing angles.]

[65. A method to configure a multi-beam apparatus for observing a surface of a sample, comprising steps of:

using an image-forming means of a source-conversion unit to deflect a plurality of beamlets from an electron source to form a plurality of first virtual images thereof respectively;

using a transfer lens to image said plurality of first virtual images onto an intermediate image plane and forms a plurality of second real images respectively;

placing a field lens on said intermediate image plane to bend said plurality of beamlets; and using an objective lens to image said plurality of second real images onto said surface and form a plurality of probe spots thereon.]

[66. The method according to claim 65, further comprising a step of changing deflection angles of said plurality of beamlets due to said image-forming means to vary pitches of said plurality of probe spots.]

[67. The method according to claim 65, further comprising a step of setting deflection angles of said plurality of beamlets due to said image-forming means and bending angles of said plurality of beamlets due to said field lens so that said plurality of beamlets lands on said surface with same or substantially same landing angles.]

[68. The method according to claim 67, further comprising a step of varying said deflection angles to equally change said landing angles.]

[69. The method according to claim 67, further comprising a step of using a deflection scanning unit to tilt said plurality of beamlets to equally change said landing angles.]

[70. The method according to claim 67, further comprising a step of using a beamlet-tilting deflector to tilt said plurality of beamlets to equally change said landing angles.]

[71. The method according to claim 65, further comprising a step of configuring said objective lens with a first magnetic lens and a first electrostatic lens.]

[72. The method according to claim 71, further comprising a step of changing a ratio of focusing powers of said first magnetic lens and said first electrostatic lens to select an orientation of said plurality of probe spots.]

[73. The method according to claim 65, further comprising a step of configuring said transfer lens with a second magnetic lens and a second electrostatic lens.]

[74. The method according to claim 73, further comprising a step of changing a ratio of focusing powers of said second magnetic lens and said second electrostatic lens to select an orientation of said plurality of probe spots.]

[75. The method according to claim 65, further comprising a step of configuring said field lens with a third magnetic lens and a third electrostatic lens.]

[76. The method according to claim 75, further comprising a step of changing a ratio of focusing powers of said third magnetic lens and said third electrostatic lens to select an orientation of said plurality of probe spots.]

77. An apparatus, comprising:

a source for providing a primary charged particle beam;

a source-conversion unit for dividing the primary charged particle beam into a plurality of charged particle beamlets and using which to form a plurality of images of the source respectively*, the source-conversion unit comprising a beamlet-limit means with beam-limit openings and an image-forming means with electron optics elements*;

an objective lens below said source-conversion unit for projecting the plurality of images onto a sample surface;

wherein pitches of the plurality of charged particle beamlets on the sample surface are adjustable by changing [deflection angles of the plurality of charged particle beamlets prior entering] *a distance from a deflection plane of the source-conversion unit to* the objective lens.

78. An apparatus, comprising:

a source for providing a primary charged particle beam;

*a beamlet-limit* means *with beam-limit openings* for [using] *allowing* a plurality of beamlets of the primary charged particle beam *to pass through, the plurality of beamlets being used* to form a plurality of images of the source;

an objective lens for projecting the plurality of images onto a sample surface to form a plurality of probe spots; and

*an image-forming* means *with electron optics elements* for adjusting pitches of the plurality of probe spots on the sample surface *by moving along a primary optical axis*.

79. A method for observing a sample surface, said method comprising steps of:

providing a plurality of charged particle beams with a plurality of crossovers respectively *using a source-conversion unit*;

projecting the plurality of crossovers onto the sample surface to form a plurality of probe spots thereon *using an objective lens*;

scanning the plurality of probe spots on the sample surface; and changing *a distance from a* deflection [angles of the plurality of charged particle beams] *plane of the source-conversion unit to the objective lens* such that pitches of the plurality of *probe* spots can be adjusted.

*80. A source-conversion unit comprising:*

*a beamlet-limit device with a plurality of beam-limit openings configured to allow a plurality of beamlets to pass through: and*

*an image-forming device movable along a primary optical axis and comprising a plurality of electron optics elements, wherein at least some of the plurality of electron optics are configured to deflect at least some of the plurality of beamlets towards the primary optical axis.*

*81. The source-conversion unit of claim 80, wherein the deflection of the at least some of the plurality of beamlets towards the primary optical axis form a plurality of virtual images of an electron source.*

*82. The source-conversion unit of claim 80, wherein the at least some of the plurality of electron optics elements are configured to deflect at least some of the plurality of beamlets at deflection angles to reduce off-axis aberrations of a plurality of probe spots.*

*83. The source-conversion unit of claim 82, wherein the plurality of probe spots have pitches that are varied together by moving the image-forming device along the primary optical axis.*

*84. The source-conversion unit of claim 82, wherein the plurality of probe spots have an orientation that is selectable by varying a ratio of focusing powers of a magnetic lens and an electrostatic lens.*

*85. The source-conversion unit of claim 82, wherein the deflection angles enable the at least some of the plurality of beamlets to land on a surface of a sample perpendicularly or substantially perpendicularly.*

*86. The source-conversion unit of claim 82, wherein the deflection angles enable the at least some of the plurality of beamlets to obliquely land on a surface of a sample with a same or substantially same landing angles.*

*87. A multi-beam apparatus comprising:*

*an electron source configured to generate a charged-particle beam along a primary optical axis:*

*a source-conversion unit comprising:*

*a beamlet-limit device with a plurality of beam-limit openings configured to allow a plurality of beamlets of the charged-particle beam to pass through, and*

*an image-forming device movable along the primary optical axis and comprising a plurality of electron optics elements, wherein at least some of the plurality of electron optics are configured to deflect at least some of the plurality of beamlets towards the primary optical axis: and*

*an objective lens configured to focus the plurality of beamlets on a surface of a sample to form a plurality of probe spots.*

*88. The multi-beam apparatus of claim 87, wherein the deflection of the at least some of the plurality of beamlets towards the primary optical axis form a plurality of virtual images of the electron source.*

*89. The multi-beam apparatus of claim 87, wherein the objective lens comprises a magnetic lens and an electrostatic lens.*

*90. The multi-beam apparatus of claim 89, wherein the magnetic lens and the electrostatic lens are configured to enable a selection of an orientation of the plurality of probe by varying a ratio of focusing powers of the magnetic lens and the electrostatic lens.*

*91. The multi-beam apparatus of claim 87, wherein the plurality of probe spots have pitches that are varied together by moving the image-forming device along the primary optical axis.*

*92. The multi-beam apparatus of claim 87, wherein the at least some of the plurality of electron optics elements are configured to deflect at least some of the plurality of beamlets at deflection angles to reduce off-axis aberrations of the plurality of probe spots.*

*93. The multi-beam apparatus of claim 92, wherein the deflection angles enable the at least some of the plurality of beamlets to land on a surface of a sample perpendicularly or substantially perpendicularly.*

*94. The multi-beam apparatus of claim 92, wherein the deflection angles enable the at least some of the plurality of beamlets to obliquely land on a surface of a sample with same or substantially same landing angles.*

*95. The multi-beam apparatus of claim 87, further comprising a deflection scanning unit positioned above a front focal plan of the objective lens.*

*96. The multi-beam apparatus of claim 95, wherein the deflection scanning unit is configured to tilt the plurality of beamlets to obliquely land on the surface with a same or substantially the same landing angles.*

*97. The multi-beam apparatus of claim 87, further comprising a beamlet-tilting deflector positioned between the source-conversion unit and a front focal plan of the objective lens.*

*98. The multi-beam apparatus of claim 97, wherein the beamlet-tilting deflector is configured to tilt the plurality of beamlets to obliquely land on the surface with a same or substantially the same landing angles.*

*99. A method to configure a multi-beam apparatus for observing a surface of a sample, the method comprising:*

*forming a plurality of virtual images of an electron source using an image-forming device with electron optics elements, wherein the virtual images are used to form a plurality of probe spots on the surface; and*

*moving the image forming device along a primary axis to vary pitches of the plurality of probe spots.*

*100. The method of claim 99, further comprising forming the plurality of probe spots on the sample using an objective lens to image the plurality of virtual images on the surface.*

* * * * *